(12) United States Patent
Cimino et al.

(10) Patent No.: US 6,433,343 B1
(45) Date of Patent: Aug. 13, 2002

(54) DEVICE AND METHOD FOR PHOTOACTIVATION

(75) Inventors: George D. Cimino, Richmond; Romilly John Simms, Palo Alto, both of CA (US)

(73) Assignee: Cerus Corporation, Concord, CA (US)

( * ) Notice: Subject to any disclaimer, the term of this patent is extended or adjusted under 35 U.S.C. 154(b) by 0 days.

(21) Appl. No.: 09/349,646

(22) Filed: Jul. 8, 1999

Related U.S. Application Data

(63) Continuation of application No. 08/664,992, filed on Jun. 13, 1996, which is a continuation of application No. 08/380,154, filed on Jan. 30, 1995, which is a continuation of application No. 08/150,940, filed on Nov. 10, 1993, which is a continuation-in-part of application No. 07/844,790, filed on Mar. 2, 1992, now Pat. No. 5,288,605.

(51) Int. Cl.[7] .................................. A61L 2/10
(52) U.S. Cl. .............. 250/455.11; 250/504 R; 250/492.1
(58) Field of Search .................. 250/455.1, 504 R, 250/492.1

(56) References Cited

U.S. PATENT DOCUMENTS

| | | |
|---|---|---|
| 1,961,700 A | 6/1934 | Moehler |
| 2,056,614 A | 10/1936 | Moehler |
| 2,169,081 A | 4/1939 | James |
| 2,212,330 A | 8/1940 | Thomas |
| 3,776,694 A | 12/1973 | Leittl |
| 3,852,032 A | 12/1974 | Urbach |
| 4,124,598 A | 11/1978 | Hearst et al. |
| 4,169,204 A | 9/1979 | Hearst et al. |
| 4,196,281 A | 4/1980 | Hearst et al. |
| 4,250,390 A * | 2/1981 | Nicholson ............... 250/504 R |
| 4,312,883 A | 1/1982 | Baccichetti et al. |
| 4,321,919 A | 3/1982 | Edelson |
| 4,398,031 A | 8/1983 | Bender et al. |
| 4,421,987 A | 12/1983 | Herold |
| 4,535,247 A | 8/1985 | Kurtz |
| 4,545,987 A | 10/1985 | Giles |
| 4,573,962 A | 3/1986 | Troutner |
| 4,613,322 A | 9/1986 | Edelson |
| 4,621,195 A | 11/1986 | Larsson |
| 4,642,171 A | 2/1987 | Sekine et al. |
| 4,645,649 A | 2/1987 | Nagao |
| 4,684,521 A | 8/1987 | Edelson |
| 4,692,138 A | 9/1987 | Troutner et al. |
| 4,693,981 A | 9/1987 | Wiesehaln |
| 4,726,949 A | 2/1988 | Miripol |
| 4,727,027 A | 2/1988 | Wiesehahn et al. |

(List continued on next page.)

FOREIGN PATENT DOCUMENTS

| | | |
|---|---|---|
| WO | WO 90/07952 | 7/1990 |
| WO | WO91/03933 | 4/1991 |
| WO | WO 91/06843 | 5/1991 |

(List continued on next page.)

OTHER PUBLICATIONS

U.S. patent application Ser. No. 08/871,590, filed Jun. 6, 1997.

Albarella et al. "Monoadduct forming photochemical reagents for labeling nucleic acids for hybridization", Nuc. Acids. Res. 17:4293–4308.

(List continued on next page.)

*Primary Examiner*—Jack Berman
(74) *Attorney, Agent, or Firm*—John W. Tessman

(57) ABSTRACT

Methods and compositions are described for treating contaminants in material intended for in vivo use, and in particular blood and blood products for human use. Contaminants in blood cell preparations are inactivated prior to long term storage and transfusion. Inactivation is accomplished using a device having a unique temperature control design.

8 Claims, 9 Drawing Sheets

U.S. PATENT DOCUMENTS

| | | | |
|---|---|---|---|
| 4,748,120 A | 5/1988 | Wiesehahn | |
| 4,769,131 A | 9/1988 | Noll et al. | |
| 4,866,282 A | 9/1989 | Miripol | |
| 4,878,891 A | 11/1989 | Judy | |
| 4,915,683 A | 4/1990 | Sieber | |
| 4,952,812 A | 8/1990 | Miripol | |
| 4,960,408 A | 10/1990 | Klainer et al. | |
| 5,030,200 A | 7/1991 | Judy et al. | |
| 5,041,078 A | 8/1991 | Matthews et al. | |
| 5,114,670 A | 5/1992 | Duffey | |
| 5,120,649 A | 6/1992 | Horowitz et al. | |
| 5,133,932 A | 7/1992 | Gunn et al. | |
| 5,166,528 A | 11/1992 | Le Vay | |
| 5,184,020 A | 2/1993 | Hearst | |
| 5,185,532 A | 2/1993 | Zabsky et al. | |
| 5,216,251 A | 6/1993 | Matschke | |
| 5,229,081 A | 7/1993 | Suda | |
| 5,288,605 A | 2/1994 | Lin | |
| 5,288,647 A | 2/1994 | Zimlich, Jr. et al. | |
| 5,304,113 A | 4/1994 | Sieber et al. | |
| 5,342,752 A | 8/1994 | Platz et al. | |
| 5,372,929 A | 12/1994 | Cimino | |
| 5,399,719 A | 3/1995 | Wollowitz et al. | |
| 5,418,130 A | 5/1995 | Platz | |
| 5,459,030 A | 10/1995 | Lin | |
| 5,459,322 A | 10/1995 | Warkentin | |
| 5,503,721 A | 4/1996 | Hearst et al. | |
| 5,593,823 A | 1/1997 | Wollowitz et al. | |
| 5,652,096 A | 7/1997 | Cimino et al. | |
| 5,762,867 A | 6/1998 | D'Silva | |

FOREIGN PATENT DOCUMENTS

| | | |
|---|---|---|
| WO | WO 92/11060 | 7/1992 |
| WO | WO 93/17553 | 9/1993 |
| WO | WO 94/03054 | 2/1994 |

OTHER PUBLICATIONS

Alter et al., "Photochemical Decontamination of Blood Components Containing Hepatitis B and Non–A, Non–B Virus," The Lancet (ii:1446–1450) (1988).

Artuc, M., et al. "Reversible binding of 5–and 8–methoxypsoralen to human serum proteins (albumin) and to epidermis in vitro"101:669–677 (1979).

Belogurov and Zavil'gel'skii "Mechanism of the inactivation of the photosensitizer 8–Methoxypsoralen on bacteria and bacteriophages" Sovgenet 14:219–223 (1978).

Bender D. et al., "Psoralen synthesis improvements in furano ring formation application to the synthesis of 4,5'8–trimethylpsoralen," J. Org. Chem. 44:13 2176–2180 (1979).

Bordin, F. et al. "5'Methylangelicin: a new highly photosensitizing angular furocoumarin" Experientia 35:1567 (1979).

Bridges, B.A. "8–methoxypsoralen and radiation damage in bacteria" Int'l. J. Rad. Bio. 20:185 (date not available).

Buchholz, D.H. et al. "Bacterial proliferation in platelet products stored at room temperature" New Eng. J. of Med. 285:429–433 (1971).

Buchholz, D.H. et al. "Detection and quantitation of bacteria in platelet products stored at ambient temperature" Transfusion 13:268–285 (1973).

Caffieri, S. et al. "Photocycloaddition of 4,5'–Dimethylangelicin to cytosine in the photoreaction with DNA: Isolatinof adduct" Medecine Bio. Envir. 11:386 (1983).

Carmen, R. "The selection of plastic materials for blood bags" Transfusion Med. Rev. 7:1 (1993).

Cimino et al. "Psoralens as Photoactive Probes of Nucleic Acid Structure and Function: Organic Chemistry, Photochemistry, and Biochemistry," Ann. Rev. Biochem. 54:1151–1193 (1985).

Cimino, G. et al. "Wavelength dependence for the photoreversal of a psoralen–DNA cross–link" Biochem. 25:3013 (1986).

Dall'Acqua et al. "Structure activity studies on the dark and photochemical interaction between methylangelicins and DNA" Medicine Biol. Envir. 9:303 (1981).

Dall'Acqua et al. "Monofunctional 3,4–and 4',5'—Photocycloadducts between 4, 5'–dimethylangelicin and thymine" Photochem. Photobio. 37:373 (1983).

Dall'Acqua et al. "New monofunctional reagents for DNA as possible agents for the photochemotherapy of psoriasis" Deriviatives of 4,5'dimethylangelicin J. Med. Chem 24:178 (1984).

Dodd et al., "Inactivation of viruses in platelet suspensions that retain their in vitro characteristics: comparison of psoralen–ultraviolet A and merocyanine 540 visible light methods," Transfusion 31:483–490 (1991).

Dodd, R. Y. "Will blood products be free of infectious agents?" Nance S.J. ed. Transfusion Med. in the 1900's AABB (1990).

Ericson and Wollenzien "Use of reverse transcription to determine the exact locations of psoralen photochemical crosslinks in RNA" Analytical Biochem. 174:215–223 (1988).

Friedman L and Stromberg R. "Viral inactivation and reduction in cellular blood products," Rev. Fr. Transfus. Hemobiol. 36:83–91 (1993).

Goldenberg et al. "Synthesis and Properties of Novel Psoralen Derivatives," Biochemistry 27:6971–6976 (1988).

Grana et al. "Use of 8–methoxypsoralen and ultraviolet–A pretreated concentrates to prevent Iloimmunization against class I major histocompatibility antigens" Blood 77:2530 (1991).

Groene S. and Shaw D. :Psoralen preparation of antigenically intact noninfectious rotavirus particles, J. Virol. Methods 38 93–102 (1992).

Grossman, B.J. et al. "Screening blood donors for gastrointestinal illness: a strategy to eliminate carriers fo Yersinia enterocoliticia" Transfusion 31:500(1991).

Guitto, G. et al. "Synthesis of some photosensitizing methylangeiicins, as monofunctional reagents for DNA" Eur. J. Med. Chem–Shim Ther. 16:489 (1981).

Guiotto et al. "6–methylangelicins: A new series of potential photochemotherapeutic agents for the treatment of psoriasis" J. Med. Chem. 27:959–967.

Hanson, C.V. "Photochemical Inactivation of Viruses with Psoralens: An Overview," Blood Cells: 18:7–25 (1992).

Hass and Webb "8–methoxypsoralen effect on survival and repair of *escherichia coli* after ultraviolet irradiation: action spectra" Radiation Res. 80:170 (1979).

Heal, J.M. et al. "Fatal salmonella septicemia after platelet transfusion" Transfusion 27:2 (1987).

Hearst et al. "The Reaction of the Psoralens with Deoxyribonucleic Acid," Quart. Rev. Biophys. 17:1–44 (1984).

Hearst, J.E., and Thiry, L., "The photoactivation of an RNA animal virus, vesicular stomatitis virus, with the aid of newly synthesized psoralen derivatives," Nucleic Acids Research, 4:1339–1347 (1977).

Heindel et al. "Aminomethyl psoralens. Elctrophillic substitution of hydroxymethylphthalimide on linear furocoumarins", J. Hetero. Chem. 22:73–76 (1985).

Heinmets, et al. "Inactivation of viruses in plasma by photosensitized oxidation." *Walter Reed Research Report* WRAIR 53–55. (1955) pp. 1–16.

Horowitz, B., et al., "Inactivation of viruses in labile blood derivatives," Transfusion 25:516–522 (1985).

Hyde and Hearst, "Binding of Psoralen Derivatives to DNA and Chromatin: Influence of the Ionic Environment on Dark Binding and Photoreactivity," Biochemistry 17:1251–1252 (1978).

Isaacs et al., "A Photochemical Characterization of Reactions of Psoralen Derivatives with DNA, "Trends in Photobiology (Plenum) pp. 279–294 (1982).

Isaacs et al., "In Vitro Characterization of the Reaction of Four Psoralen Derivatives with DNA," NCI Monograph 66:21–30 (1984).

Isaacs et al. "Synthesis and Characterization of New Psoralen Derivatives with Superior Photoreactivity with DNA and RNA," Biochemistry 16:1058–1064 (1977).

Lin et al. "Use of 8–Methoxypsoralen and Long–Wavelength Ultraviolet Radiation for Decontamination of Platelet Concentrates," Blood 74:517–525 (1989).

Margolis–Nunno et al., "Virus sterilization in platelet concentrates with psoralen and ultraviolet A light in the presence of quencers" Transfusion 32:6 541–547 (1992).

Margolis–Nunno et al. "Photochemical Virus Sterilization in Platelet Concentrates with Psoralen Derivatives," Thromb. Haemostas. 65:1162 (Abstract) (1991).

Matthews, J.L., et al., "Photodynamic therapy of viral contaminants with potential for blood banking applications," Transfusion 28:81–83 (1988).

Metzelaar, M.J. "A comparative studyon the use of platelet membrane markers for the detection of platelet activation In Vitro and in clinical disorders" Studies on the Expression of Activation Markers on Human Platelets (Thesis) (1991).

Mohr, H. et al., Infusionstherapie 19:79 (1992).

Moroff et al. "Factors influencing virus inactivation and retention of platelet properties following treatment with aminomethyltrimethylpsoralen and ultraviolet A light" Blood Cells 18:43–56 (1992).

Moroff, G., et al., "The influence of irradiation on stored platelets," Transfusion 26:453–456 (1986).

Morrow et al., "Septic Reactions to Platelet Transfusions, "JAMA 266:555–558 (1991).

Murphy and Gardner "Platelet preservation–effect of storage temperature on maintenance of platelet viability—deleterious effect of refrigerated storage" New Eng. J. Med 280:1094 (1969).

Myhre, B.A. "Fatalities from blood transfusion" JAMA 244:1333 (1980).

Nair and Davis "Photochemical inhibition of poliovirus replication by 4,5'8–trimethylpsoralen plus light" Intervirology 9:65–75 (1978).

Nilsen, T. et al. "Cross–linking of viral RNA by 4'–aminomethyl–4,5',8–trimethylpsoralen HeLa cels infected with encephalomyocarditis virus and the tsG114 mutant of vesicular stomatitis virus" Virology 109 82–93 (1981).

North J. et al. "Photodynamic inactivation of retrovirus by benzoporphyrin derivative: a feline leukemia virus model" Transfusion 32:121–128 (1992).

Ou et al. "Photobinding of 8–methoxypsoralen and 5,7–dimethoxycoumarin to DNA and its effect on template activity" Biochem. 17:1047–1053 (1978).

Piette and Moore "DNA synthesis on ØX174 template damaged by proflavine and light treatment", Photochem. Photobio. 35:705–708 (1982).

Piette and Hearst "Termination sites of the in vitro nick––translation reaction DNA that had photoreacted with psoralens", *Proc. Nat'l. Acad. Sci* 80:5540–5544 (1983).

Piette and Hearst "Termination sites of the vitro DNA synthesis on psoralens phototreated signal–stranded templates", *Int. J. Radiat. Biol.* (1985) 48:381–388.

Prince, A.M., et al., "β–Propiolactone/Ultraviolet Irradiation: A review of Its Effectiveness for Inactivation of Viruses in Blood Derivatives," Reviews of Infect. Diseases 5:92–107 (1983).

Prodouz, K.N., et al., "Use of Laser U–V for Inactivation of Virus in Blood Platelets," Blood 70:589–592 (1987).

Rai, S. et al., "Dramatic Improvements in Viral Inactivation with Brominated Psoralens, Naphthalenes and Anthracenes" *Photochem. and Photobio.* (1993) 58:59–65.

Sieber, F. et al., "Invitation of friend erythroleukemia virus and friend virus—transformed cells by merocyanine 540–mediated photosensitization" Blood 73:345–350 (1989).

Stack, G., "Storage of platleet concentrate" Blood Separation and Platelet Fractionation pp. 99–125 (1991).

Tessman et al. "Photoxhemistry of the Furan–Side 8–Methoxypsoralen–Thymide Monoadduct Inside the DNA Helix. conversion to Diadduct and to Pyrone–Side Monoadduct," Biochem. 24:1669–1676 (1985).

Thompson et al., "Determination of the Secondary Structure of Drosophila Melanogaster 5 S RNA by Hydroxymethyltrimethylpsoralen Crosslinking", *J. Mol. Biol.* 147: 417–436 (1981).

Thompson et al., "Dependence of 4'–(Hydroxymethyl)–4, 5',8–trimethylpsoralen Photoaddition on the Conformation of Ribonucleic Acid", Biochemistry 21:1363–1368 (1982).

Wagner et al. "Determination of residual 4'aminomethyl–4, 5',8–trimethylpsoralen and mutagenicity testing following psorlen plus UVA treatment of platelet suspensions" Photochem. & Photobio. 57:5 819–824 (1993).

Wagner, et al. "Approaches to the reduction of viral infectivity in cellular blood components and single donor plasma" Trans. Med. Rev. V:1 18–32 (1991).

Willis and Menter, "Psoralens: A search for more effective derivatives for photochemotherapeutic regimes", *Nat. Cancer Inst. Mono.* (1985) 66:143–147.

CFR Title 29, Part 1910.1006 OSHA Regulated Carcinogen.

Stratagene Catalog.

* cited by examiner

DEVICE AND METHOD FOR PHOTOACTIVATION

The present application is a Continuation of copending application Ser. No. 08/664,992 filed on Jun. 13, 1996, which is a Continuation of application Ser. No. 08/380,154 filed on Jan. 30, 1995, which is a Continuation of application Ser. No. 08/150,940 filed on Nov. 10, 1993, which is a Continuation-in-Part of Ser. No. 07/844,790 filed Mar. 2, 1992 now U.S. Pat. No. 5,288,605 issued on Feb. 22, 1994.

FIELD OF THE INVENTION

The invention generally relates to a device and method for photoactivating new and known compounds.

BACKGROUND

Whole blood collected from volunteer donors for transfusion recipients is typically separated into its components: red blood cells, platelets, and plasma. Each of these fractions is individually stored and used to treat a multiplicity of specific conditions and disease states. For example, the red blood cell component is used to treat anemia; the concentrated platelet component is used to control bleeding; and the plasma component is used frequently as a source of Clotting Factor VIII for the treatment of hemophilia.

Ideally, all blood cell preparations should be from freshly drawn blood and then immediately transfused to the recipient. However, the logistics of operating a blood donor center preclude this possibility in the vast majority of cases. Transfusions are needed day and night and it is difficult, if not impossible, to arrange for donor recruiting at unusual hours. Consequently, modern blood donor centers must use stored blood products.

In the United States, blood storage procedures are subject to regulation by the government. The maximum storage periods for the blood components collected in these systems are specifically prescribed.

For example, whole blood components collected in an "open" (i.e. non-sterile) system must, under governmental rules, be transfused within twenty-four hours and in most cases within six to eight hours. By contrast, when whole blood components are collected in a "closed" (i.e. sterile) system the red blood cells can be stored up to forty-two days (depending upon the type of anticoagulant and storage medium used) and plasma may be frozen and stored for even longer periods.

Murphy and Gardner, New Eng. J. Med. 280:1094 (1969), demonstrated that platelets stored as platelet-rich plasma (PRP) at 22° C. possessed a better in vivo half-life than those stored at 4° C. Thus, more acceptable platelet concentrates could be transfused after storage at room temperature. Until recently, the rules allowed for platelet concentrate storage at room temperature for up to seven days (depending upon the type of storage container). However, it was recognized that the incidence of bacterial growth and subsequent transfusion reactions in the recipient increased to unacceptable levels with a seven day old platelet concentrate. Platelet concentrates may now be stored for no more than five days.

Blood bags used for platelet concentrate preparation are in themselves sterile, as are the connected satellite bags. One might believe, therefore, that it is a relatively simple matter to keep the blood preparation sterile during the manipulations needed to concentrate the platelets. However, bacteria can be introduced by at least two different means. First, if the donor is experiencing a mild bacteremia, the blood will be contaminated, regardless of the collection or storage method. Adequate donor histories and physicals will decrease but not eliminate this problem. See B. J. Grossman et al., Transfusion 31:500 (1991). A second, more pervasive source of contamination is the venepuncture.

Even when "sterile" methods of skin preparation are employed, it is extremely. difficult to sterilize the crypts around the sweat glands and hair follicles. During venepuncture, this contaminated skin is often cut out in a small "core" by a sharp needle. This core can serve to "seed" the, blood bag with bacteria that may grow and become a risk to the recipient.

Indeed, many patients requiring platelet transfusions lack host-defense mechanisms for normal clearing and destruction of bacteria because of either chemotherapy or basic hematological disease. The growth of even seemingly innocuous organisms in stored platelets can, upon transfusion, result in recipient reaction and death. See e.g. B. A. Myhre JAMA 244:1333 (1980). J. M. Heal et al. Transfusion 27:2 (1987).

The reports assessing the extent of contamination in platelets have differed in their methods, sample size, and bacterial detection schemes. D. H. Buchholz, et al., Transfusion 13:268 (1973) reported an overall level of platelet contamination of 2.4% when a large (>1000 bags) sample was examined and extensive measures were taken for bacterial culturing. While some units were heavily contaminated after just 24 hours of storage, the incidence as a whole varied according to. the age of the concentrate and increased with the widespread practice of pooling individual units; over 30% of pools were contaminated at 3 days. See also D. H. Buccholz, et al., New Eng. J. Med. 285:429 (1971). While other clinicians suggest lower numbers, recent studies indicate that septic platelet transfusions are significantly underreported. See e.g. J. F. Morrow et al. JAMA 266:555 (1991).

Pre-culturing platelets is not a solution to the bacterial contamination problem. The culture assay takes 48 hours to detect growth. Holding platelet units for an additional two days to await the results of the assay would create, ironically, a smaller margin of safety. See Table 2 in J. F. Morrow et al. JAMA 266:555 (1991). While heavily contaminated units would be detected at the outset, lightly contaminated units would be allowed to grow for two days. Older and potentially more contaminated units would end up being transfused.

Washing the blood cells (e.g. with saline) or filtering the bacteria are also not practical solutions. These techniques are time consuming and inefficient, as they can reduce the number of viable blood cells available for transfusion. Most importantly, they typically involve an "entry" into the storage system. Once an entry is made in a previously closed system, the system is considered "opened," and transfusion must occur quickly, regardless of the manner in which the. blood was collected and processed in the first place.

Nor are antibiotics a reasonable solution. Contamination occurs from a wide spectrum of organisms. Antibiotics would be needed to cover this spectrum. Many recipients are allergic to antibiotics. In addition, there is an every increasing array of drug-resistant strains of bacteria that would not be inactivated.

There has been interest recently in inactivation of pathogens in blood using photoreactive compounds, such as psoralens. Psoralens are tricyclic compounds formed by the linear fusion of a furan ring with a coumarin. Psoralens can intercalate between the base pairs of double-stranded nucleic acids, forming covalent adducts to pyrimidine bases upon absorption of long wave ultraviolet light (UVA). G. D. Cimino et al, Ann. Rev. Biochem. 54:1151 (1985). Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977). S. T. Isaacs et al., Trends in Photobiology (Plenum) pp. 279–294 (1982). J. Tessman et al.; Biochem. 24:1669 (1985). Hearst et al., U.S. Pat. Nos. 4,124,589, 4,169,204, and 4,196,281, hereby incorporated by reference.

Psoralens have been shown to inactivate viruses in some blood products. See H. J. Alter et al., The Lancet (ii:1446) (1988). L. Lin et al., J Blood 74:517 (1989). G. P. Wiesehahn et al., U.S. Pat. Nos. 4,727,027 and 4,748,120, hereby incorporated by reference, describe the use of a combination of 8-methoxypsoralen (8-MOP) and irradiation. They show that 300 ug/ml of 8-MOP together with one hour or more of irradiation with ultraviolet light can effectively inactivate viruses. However, these treatment conditions cause harm to the blood product because of energy transfer. Their approach is only feasible if the damage to cells is specifically suppressed by limiting the concentration of molecular oxygen, a difficult and expensive process.

Isopsoralens, like psoralens, are tricyclic compounds formed by the fusion of a furan ring with a coumarin. See Baccichetti et al., U.S. Pat. No. 4,312,883. F. Bordin et al., Experientia 35:1567 (1979). F. Dall'Acqua et al., Medeline Biologie Envir. 9:303 (1981). S. Caffieri et al., Medecine Biologie Envir. 11:386 (1983). F. Dall'Acqua et al., Photochem Photobio. 37:373 (1983). G. Guiotto et al., Eur. J. Med. Chem-Chim. Ther. 16:489 (1981). F. Dall'Acqua et al. J. Med. Chem. 24:178 (1984). Unlike psoralens, the rings of isopsoralen are not linearly annulated. While able to intercalate between the base pairs of double-stranded nucleic acids and form covalent adducts to nucleic acid bases upon absorption of longwave ultraviolet light, isopsoralens, due to their angular geometry, normally cannot form crosslinks with DNA. See generally, G. D. Cimino et al., Ann. Rev. Biochem. 54:1151 (1985).

There are devices presently employed which emit ultraviolet radiation for activating psoralens and other photoactivated compounds. U.S. Pat. No. 5,184,020, to Hearst, et al., discloses such a device for photoactivating psoralens. However, the disclosed device is structured for the irradiation of samples in tube like vessels. It does not disclose a device for use on blood bags. Further, although the patent discloses a cooling system for the irradiated samples, this system would not work for blood bags because it depends on the circulation of fluid around the sample vessels.

Other devices are not appropriate for activating psoralens, but can be used for other purposes with blood bags. For example, U.S. Pat. Nos. 4,726,949 and 4,866,282, to Miripol, disclose such an irradiation device for use in preventing alloimmunization. This device is not practical for use in laboratories which will process large quantities of blood for sterilization. The device only supports one blood container, which would bottleneck the processing of blood. (See FIG. 1, ref. no. 10, of either Miripol patent). Further, it provides radiation of wavelength from 280 to 320 nanometers, including the 313 band, (see claim 1 of the '282 patent) at which nucleic acids absorb radiation and could be damaged. The UVB range can also destroy platelet function. The Miripol patents state that UV-A range sources "do not provide good reduction of the lymphocyte alloimmunization effect." Column 2, line 61–64, of '949. Finally, the Miripol patents disclose the use of only one means for cooling the system during irradiation, an exhaust fan. The goal in those patents is to maintain the heat at 31 degrees C or less. Column 3, line 44–46. However, platelets are currently stored at 22–24 degrees C. G. Stack and L. Snyder, "Storage of Platelet Concentrate," Blood Separation and Platelet Fractionation, pp. 9–125 (1991 Wiley-Liss, Inc.)

Last, there are devices disclosed which would neither be appropriate for activating psoralens nor for other uses on blood products. U.S. Pat. No. 4,421,987, to Herold, discloses an apparatus for irradiating dental objects which employs radiation in the spectral range of 400 to 500 nm, for bleaching treatment of dental parts. The device is fitted with a selective reflector which reflects from the total radiation emitted by the lamp only the spectral portion lying in the desired spectral range (approximately 400 to 500 nm) while transmitting or passing the portion of the radiation lying outside this desired spectral range. The device also has a temperature control system, employing the combination of a blower with an absorption filter which, like the reflector, removes radiation outside of the desired spectral range. This apparatus is not suited for the present purpose of a photo-decontamination treatment, because it is designed for use with wavelengths of light which are damaging to some blood components, while it removes wavelengths necessary to activate certain ph6toreactive compounds. Further, it is not equipped with a temperature maintaining system which would keep the temperature of blood samples low enough to prevent damage.

In sum, there is a need for a means of inactivating bacteria in blood components prior to storage and transfusion in a way that lends itself to use in a closed system, such as a system of blood bags. This approach must be able to handle a high volume of blood and a variety of organisms while efficiently controlling the temperature and avoiding harm to the blood product or the transfusion recipient.

SUMMARY OF THE INVENTION

The present invention relates to a device and method for photoactivating new and known compounds. The present invention further contemplates devices for binding new and known compounds to nucleic acid. Specifically, the present invention contemplates a device for photoactivating new and known compounds so that they bind to and inactivate bloodborne pathogens. In accordance with the present invention, a nucleic acid binding compound is selectively employed to treat contamination by microorganisms.

In one embodiment, the present invention contemplates: a photoactivation device for inactivating pathogens in blood products, comprising: a housing; means for providing electromagnetic radiation to cause activation of at least one photoreactive compound, contained within said housing; means for supporting a plurality of blood bags, containing said photoreactive compound, at a fixed distance from said radiation providing means during said activation, comprising a lower ultraviolet light transparent plate assembly within said housing, upon which said blood bags can rest; and an upper ultraviolet light transparent plate assembly, positioned above said lower plate assembly, said upper and lower plate assemblies defining a channel, closed off from significant exchange with air originating from outside said housing during irradiation, in which air can be circulated to cool said blood bags. In another embodiment, said lower plate assembly comprises a top and a bottom plate and an air circulation chamber between said top and bottom plates, open to said channel to allow air exchange between said air circulation chamber and said channel. In a preferred embodiment, the device further comprises: first temperature maintaining means, comprising: means for blowing air from outside, through said housing, between said irradiation providing means and said plate assemblies, positioned within and adjacent to said housing, for cooling said irradiation providing means; and second temperature maintaining means, positioned within said housing, for circulating cooled air through said air circulation chamber and said channel, comprising: a heat exchanger, between said plate assemblies, for absorbing heat from air present in said housing, and; means for circulating air, positioned in a fixed relationship to said heat exchanger. In one embodiment, said heat exchanger comprises a conduit having an inlet port and an outlet port so that temperature control liquid may enter and exit. In a preferred embodiment, said upper and lower plate assemblies are separated by between approximately 1 and 10 cm. However, it is preferred that when said blood bags rest upon said lower plate assembly, said upper plate assembly does not contact said blood bags.

Because of the benefits of rapid processing, in one contemplated embodiment said lower plate assembly is of dimensions sufficient to support six of said blood bags. Said blood bag supporting means may further comprise means to position a plurality of attachments connected to said blood bags, so that said attachments do not significantly reduce the intensity of radiation to said blood bags, including tubing for transferring a blood product into or out of said blood bags and a blood product storage bag. The device may further comprise means for shaking said blood bag supporting means, positioned adjacent to said blood bag supporting means, for providing mixing of a sample in a blood bag during irradiation. The present invention contemplates that said lower plate. assembly has a ridged upper surface to maintain the position of said blood bags during shaking.

In a preferred embodiment, said housing comprises material which blocks said electromagnetic radiation so that users are shielded from said electromagnetic radiation during said activation. Also contemplated is a means for controlling said radiation providing means, which may comprise a plurality of detectors, positioned around said radiation providing means, to measure said electromagnetic radiation; and a feedback control, connected to said detectors, which shuts off said radiation providing means at a desired output of radiation detected by said detectors. Preferably, the intensity of radiation provided by said radiation providing means is at least 15 mW/cm$^2$, and said radiation providing means has a high end wavelength cutoff above 400 nanometers. Additionally, it is contemplated that the upper and lower plate assemblies are comprised of material. which filters said electromagnetic radiation to provide a low end wavelength cutoff below 320 nanometers.

The radiation providing means may further comprise a top bank and a bottom bank of light sources, said top bank being located above said upper plate assembly, and said bottom bank being located below said lower plate assembly. Reflecting means, adjacent to said top bank and said bottom bank of light sources, are also contemplated, which reflect electromagnetic radiation from said light sources toward said blood bag supporting means.

In an alternative embodiment of the present invention, a photoactivation device is contemplated for treating photoreactive compounds, comprising: an opaque housing; means for providing electromagnetic radiation to cause activation of at least one photoreactive compound, within said housing; means for supporting a plurality of blood bags at a fixed distance from said radiation providing means during said activation, comprising a lower ultraviolet light transparent plate assembly, within said housing, upon which said blood bags can rest; an upper ultraviolet light transparent plate assembly, positioned above said lower plate assembly, said upper and lower plate assembly defining a channel, closed off from significant exchange with air originating from outside said housing during irradiation, through which air can be circulated to cool said blood bags; first temperature maintaining means, comprising: means for blowing air from outside, through said housing, between said irradiation providing means and said plate assemblies, positioned within and adjacent to said housing, for cooling said irradiation providing means; and second temperature maintaining means, positioned within said housing, for circulating cooled air through said channel, comprising: a heat exchanger, between said plate assemblies, for absorbing heat from air present in said housing; and means for circulating air, positioned in a fixed relationship to said heat exchanger, for circulating cooled air from said heat exchanger through said channel. In one embodiment, said heat exchanger comprises a conduit having an inlet port and an outlet port so that temperature control liquid may enter and exit. Said lower plate assembly may be comprised of a top and a bottom plate, and an air circulation chamber between said top and bottom plates. In this embodiment, said means for circulating air circulates air through said air circulation chamber.

It is contemplated that said upper and lower plate assemblies are separated by between approximately 1 and 10 cm. However, in a preferred embodiment, when said blood bags rest upon said lower plate assembly, said upper plate assembly does not contact said blood bags. Also contemplated is a lower plate assembly of dimensions sufficient to support six of said blood bags. It is contemplated that the blood bag supporting means further comprises means to position a plurality of attachments connected to said blood bags, so that said attachments do not significantly reduce the intensity of radiation to said blood bags. Some such attachments comprise tubing for transferring a blood product into or out of said blood bags and a blood product storage bag. The present invention further contemplates means for shaking said blood bag supporting means, positioned adjacent to said blood bag supporting means, for providing mixing of a sample in a blood bag during irradiation. In one embodiment, said lower plate assembly has a ridged upper surface to maintain the position of said blood bags during said shaking.

The present invention contemplates a photoactivation device comprising means for controlling said radiation providing means. The means for controlling said radiation providing means may comprise: a plurality of detectors, positioned around said radiation providing means, to measure said electromagnetic radiation; and a feedback control, connected to said detectors, which shuts off said radiation providing means at a desired output of radiation detected by said detectors. In a preferred embodiment, the intensity of radiation provided by said radiation providing means is at least 15 mW/cm$^2$ and said radiation providing means has a high end wavelength cutoff above 400 nanometers.

In one embodiment, said plate assemblies are comprised of material which removes blood product damaging wavelengths of radiation from said electromagnetic radiation. Specifically, it is contemplated that said material filters said electromagnetic radiation to provide a low end wavelength cutoff below 320 nanometers. It is also contemplated that said radiation providing means comprises a top bank and a bottom bank of light sources, said top bank being located above said upper plate assembly, and said bottom: bank being located below said lower plate assembly. Reflecting means may be positioned adjacent to said top bank and said bottom bank of light sources, which reflect electromagnetic radiation from said light sources toward said blood bag supporting means.

The present invention also contemplates a method for photoactivating photoreactive compounds, comprising: supporting a plurality of blood bags, containing one or more photoreactive compounds, at a fixed distance from a fluorescent source of electromagnetic radiation; irradiating said plurality of blood bags simultaneously with electromagnetic radiation having a wavelength cutoff at approximately 320 nm, from said fluorescent source to cause activation of at least one of said photoreactive compounds; and maintaining the temperature of said blood bags at approximately room temperature during said activation, by cooling air and circulating cooled air around said blood bags in a closed system. Preferably, the fluorescent source of electromagnetic radiation delivers an intensity of electromagnetic radiation greater than 1 mW/cm$^2$ to said blood bags.

DESCRIPTION OF THE INVENTION

Figure 1:
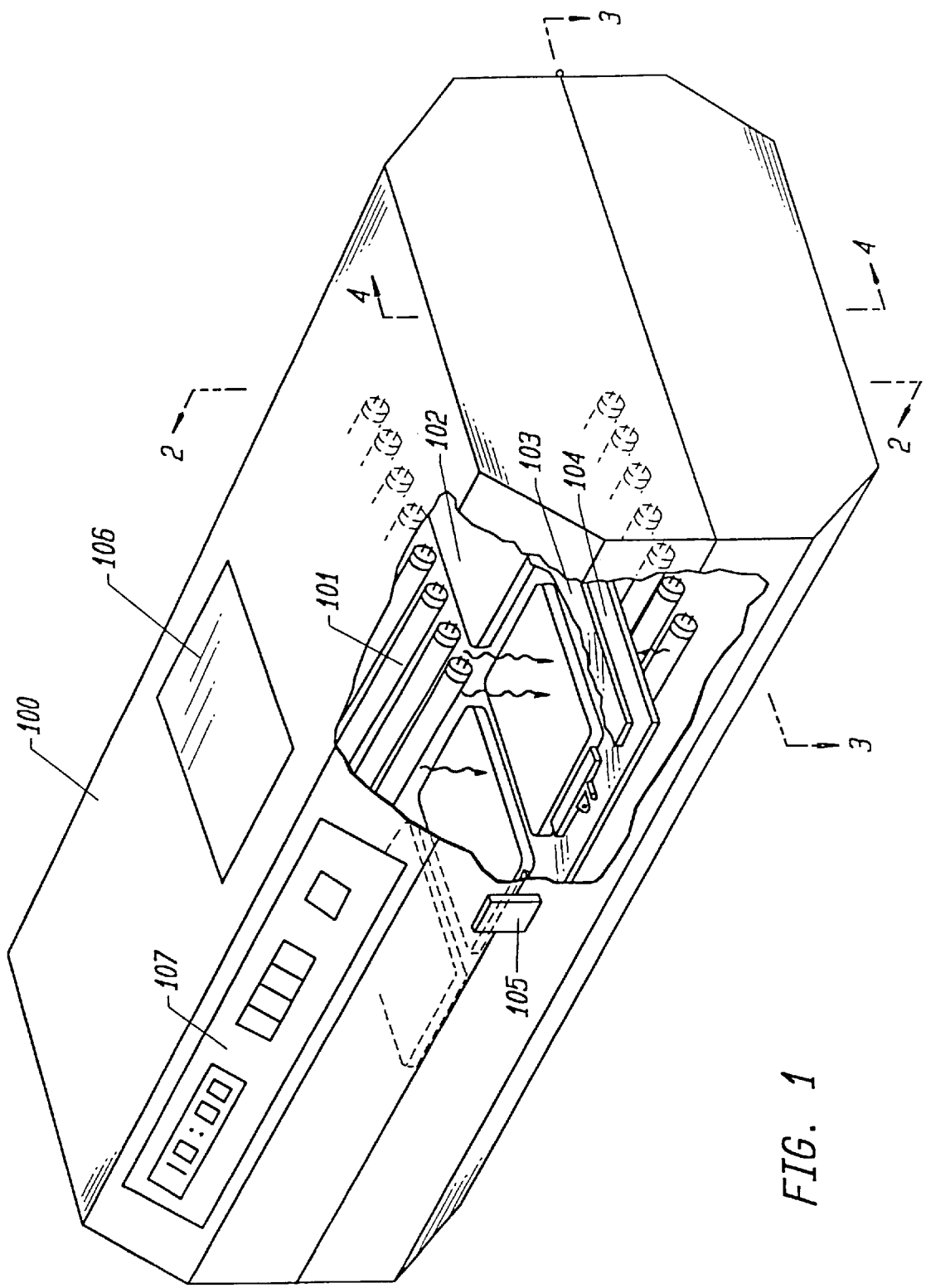
FIG. 1 is a perspective view of one embodiment of the device of the present invention in the closed position.

The present invention relates to a device and method for photoactivating new and known compounds.

As noted previously, whole blood is collected and typically separated into red blood cells, platelets, and plasma. Each of these fractions are individually stored under specific conditions prior to in vivo use. In many cases, the extent of contamination is related to the storage time because of growth. A process that inactivated microorganisms at the time of blood collection would be expected to prevent growth during storage.

TABLE 1

Photoreactive Compounds

Actinomycins
Anthracyclinones
Anthramycin
Benzodipyrones
Fluorenes and fluorenones
Furocoumarins
Mitomycin

TABLE 1-continued

Photoreactive Compounds

Monostral Fast Blue
Norphillin A
Many organic dyes not specifically listed
Phenanthridines
Phenazathionium Salts
Phenazines
Phenothiazines
Phenylazides
Quinolines
Thiaxanthenones "Photoactivation compounds" (or "photoreactive compounds") defines a family of compounds that undergo chemical change in response to electromagnetic radiation (Table 1). One species of photoreactive compounds described herein is commonly referred to as the furocoumarins. The furocoumarins belong to two main categories: 1) psoralens [7H-furo(3,2-g)-(1)-benzopyran-7-one, or ∂-lactone of 6-hydroxy-5-benzofuranacrylic acid], which are linear:

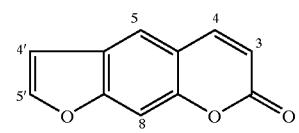

and in which the two oxygen residues appended to the central aromatic moiety have a 1, 3 orientation, and further in which the furan ring moiety is linked to the 6 position of the two ring coumarin system, and 2) the isopsoralens [2H-furo(2,3-h)-(1)-benzopyran-2-one, or ∂-lactone of 4-hydroxy-5-benzofuranacrylic acid], which are angular:

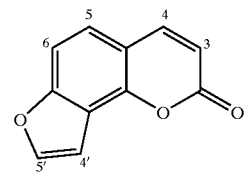

in which the two oxygen residues appended to the central aromatic moiety have a 1, 3 orientation, and further in which the furan ring moiety is linked to the 8 position of the two ring coumarin system. Psoralen derivatives are derived from substitution of the linear furocoumarin at the 3, 4, 5, 8, 4', or 5' positions, while isopsoralen derivatives are derived from substitution of the angular furocoumarin at the 3, 4, 5, 6, 4', or 5 positions.

In one embodiment, the present invention contemplates inactivating blood products after separation but before storage In this embodiment, a nucleic acid binding compound is selectively employed to treat contamination by microorganisms.

In one embodiment, the nucleic acid binding compound is selected from the group comprising furocoumarins. In a preferred embodiment, the furocoumarin is a psoralen or isopsoralen.

The inactivation method of the present invention provides a method of inactivating single cell and multicellular. organisms, and in particular, bacteria, fungi, mycoplasma and protozoa. In contrast to previous approaches, the method of the present invention does not cause harm to the blood product. There is no significant damage to cells and, therefore, no need to limit the concentration of molecular oxygen.

The present invention contemplates using much lower concentrations of nucleic acid binding compounds than previously employed. For example, the present invention contemplates using 8-MOP at concentrations of 30 ug/ml or less. Indeed, a preferred concentration of 8-MOP for bacterial decontamination in platelet concentrates is 3 ug/ml or less, i.e. a one hundred-fold lower concentration than employed by G. P. Wiesehahn et al., supra.

The present invention, furthermore, contemplates using much lower doses of irradiation than previously described. This is accomplished with lower intensity irradiation sources, with wavelength cutoff filters (see below), and/or shorter irradiation times. In a preferred embodiment, the time of irradiation is variable and controlled from 1 second to 99 minutes, in one second increments.

While it is not intended that the present invention be limited by the theory of inactivation, the use of lower compound concentrations and irradiation doses comes from an understanding that, where the present invention is applied to the decontamination of a single cell or multicellular organism (as opposed to a virus), a lower level of nucleic acid binding will achieve inactivation. In addition, it is recognized that it is not essential that inactivation be complete. That is to say, partial inactivation will be adequate as long as the viable portion is unable, within the storage period, to grow to levels sufficient to cause disease.

To appreciate that, in any given case, an inactivation method may or may not achieve complete inactivation, it is useful to consider a specific example. A bacterial culture is said to be sterilized if an aliquot of the culture, when transferred to a fresh culture plate and permitted to grow, is undetectable after a certain time period. The time period and the growth conditions (e.g. temperature) define an "amplification factor". This amplification factor along with the limitations of the detection method (e.g. visual inspection of the culture plate, for the appearance of a bacterial colony) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the method appears to be completely effective (and above which the method is, in fact, only partially effective).

This interplay between the amplification factor of an assay and the threshold that the detection method defines, can be illustrated. For example, bacterial cells can be applied to a plate; the detection method is arbitrarily chosen to be visual inspection. Assume the growth conditions and time are such that an overall amplification of $10^4$ has occurred. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective. Given the amplification factor of $10^4$ and a detection threshold of $10^6$, the sensitivity limit would be 100 bacterial cells; if less than 100 viable bacterial cells were present in the original aliquot of the bacterial culture after the sterilization method is performed, the culture would still appear to be sterilized.

Such a situation is common for bacterial growth assays. The sensitivity of the assay is such that viable bacterial cells are present but the assay is unable to detect them. This may explain, at least in part, the variability in results obtained by researchers attempted to determine the extent of bacterial contamination of blood products. See D. H. Buchholz, et al., Transfusion 13:268 (1973), wherein such variability is discussed.

It should be noted that, in many countries, contamination of blood products by cellular organisms is more pervasive and, therefore, more serious than viral contamination. For example, in South America, the most important blood-borne organism is T. cruzi which is the etiologic agent of Chagas disease. Approximately 16–18 million people are infected in the Americas (including 11% of the population of Chile). It is contemplated that the decontamination method of the present invention is well-suited for inactivation of this protozoa.

The present invention contemplates devices and methods for photoactivation and specifically, for activation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause activation of at least one photoreactive compound; b) means for supporting a plurality of blood products at a fixed distance from the radiation providing means during activation; and c) means for maintaining the temperature of the blood products within a desired temperature range during activation. The present invention also contemplates methods, comprising: a) supporting a plurality of blood product containers, containing one or more photoreactive compounds, at a fixed distance from a fluorescent source of electromagnetic radiation; b) irradiating the plurality of blood products simultaneously with said electromagnetic radiation to cause activation of at least one photoreactive compound; and c) maintaining the temperature of the blood products within a desired temperature range during activation.

The present invention contemplates devices and methods for photoactivation and specifically, for inactivation of pathogens contaminating blood products by activation of photoreactive compounds. The major features of one embodiment of the device of the present invention involve: A) an inexpensive source of ultraviolet radiation at a fixed distance from the means for supporting the sample vessels, B) rapid photoactivation, C) large sample processing, D) temperature control of the irradiated samples, E) inherent safety and F) sample containers.

A. Electromagnetic Radiation Source

A preferred photoactivation device of the present invention has an inexpensive source of ultraviolet radiation at a fixed distance from the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source, by virtue of filters or other means, does not allow passage of radiation with wavelengths shorter than a particular wavelength (e.g. 320 nm), it is said to have a low end "cutoff" at that wavelength (e.g. "a short wavelength cutoff at 320 nanometers"). Similarly, when a radiation source allows only passage of radiation with wavelengths shorter than a particular wavelength (e.g. 360 nm), it is said to have a high end "cutoff" at that wavelength (e.g. "a long wavelength cutoff at 360 nanometers").

For any photochemical reaction it is desired to eliminate or at least minimize any deleterious side reactions. Some of these side reactions can be caused by the excitation of endogenous chromophores that may be present during the photochemical activation procedure. In a system where only nucleic acid and psoralen are present, the endogenous chromophores are the nucleic acid bases themselves. Restricting the activation process to wavelengths greater than 320 nm minimizes direct nucleic acid damage since there is very little absorption by nucleic acids at wavelengths longer than 313 nm.

In blood products, the nucleic acid is typically present together with additional biological chromophores. If the biological fluid is just protein, the 320 nm short wavelength cutoff will be adequate for minimizing side reactions (aromatic amino acids do not absorb at shorter wavelengths than 320 nm). If the biological fluid includes cells and/or cellular constituents, there will be many other chromophores, including hemes and flavins.

Hemes are abundant in blood products where they arise from the lysis of red cells. Flavins, like hemes, are required for metabolic respiration. Both of these endogenous chromophores will cause damage to cells if excited by photoirradiation.

Hemes have three principle absorption bands: two are in the red region of the visible spectrum; the other is centered about 400 nm. Flavins have two principle absorption peaks: one at 450 nm and the other at 370 nm.

In view of the presence of these endogenous chromophores in blood products, it is intended that in one embodiment of the device of the present invention the device is designed to allow for irradiation within a small range of specific and desirable wavelengths, and thus avoid damage to cells caused by energy transfer. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths longer than 400 nm. This, however, only provides a long wavelength cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmit only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. It offers stability in intense sources. Other salts are known to one skilled in the art. Aperture or reflector lamps may also be used to achieve specific wavelengths and intensities.

When ultraviolet radiation is herein described in terms of irradiance, it is expressed in terms of intensity flux (milliwatts per square centimeter or "$mW/cm^2$"). "Output" is herein defined to encompass both the emission of radiation (yes or no; on or off) as well as the level of irradiance. In a preferred embodiment, intensity is monitored at least 4 locations: with at least 2 for each side of the plane of irradiation. In one embodiment, the monitors are photodiodes, each positioned to measure the output of one or more sources of radiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, "fixed distance" is defined as a constant distance between a point in the plane which the means for supporting a plurality of blood bags defines and a point within the light source. It is known that light intensity from a point source is inversely related to the square of the distance from the point source. Thus, small changes in the distance from the source can have a drastic impact on intensity. Since changes in intensity can impact photoactivation results, the present invention contemplates the use of an extended bar of lamps for a source of radiation. Extended bar lamps minimize the effect of small distance changes on intensity of radiation, providing reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure, of more than one sample, of appropriate intensity for rapid photoactivation. The geometry of a preferred device of the present invention involves multiple sources of linear lamps as opposed to single point, sources. In addition, there are several reflective surfaces and several absorptive surfaces. Reflective surfaces can help to even out the exposure of light to each of a plurality of samples. Because of this complicated geometry, changes in the location or number of the lamps relative to the position of the samples to be irradiated are to be avoided in that such changes will result in intensity changes and variability in intensity exposure to multiple samples.

Another consideration in obtaining uniform light exposure is provision for attachments to samples containers during irradiation. The present invention contemplates attachments such as tubing, valves, blood product storage bags, and any other apparatus commonly attached to bags containing blood products. This avoids blocking of light by the attachments. In one embodiment, blood bag supporting means has means to position a plurality of attachments connected to said blood bags, so that said attachments do not significantly reduce the intensity of radiation to said blood bags.

It is useful that an irradiation device deliver the same intensity of radiation to a sample whether there are several samples or just a single sample being irradiated at once. The present invention contemplates the use of parabolic reflector grids which may be positioned between the light sources and the sample to be irradiated. These grids direct light passing through, to reduce scatter of light and to avoid. decreases in the light impinging on samples when more than one sample is irradiated at the same time.

In another embodiment, the present invention contemplates the use of a shaking means, such as a shaker or agitator, to mix samples during irradiation. This mixing may have an averaging effect on the radiation received by sample material in different parts of the bag. Without intending to be limited by any mechanism by which shaking effects irradiation predictability, it is contemplated that sample material is moved throughout the bag during irradiation by shaking, thereby exposing each part of the sample to many different positions to receive radiation. If variations in the intensity of radiation exist in different areas of the bag, movement would act to reduce the variation in intensity within the sample.

Figure 8:
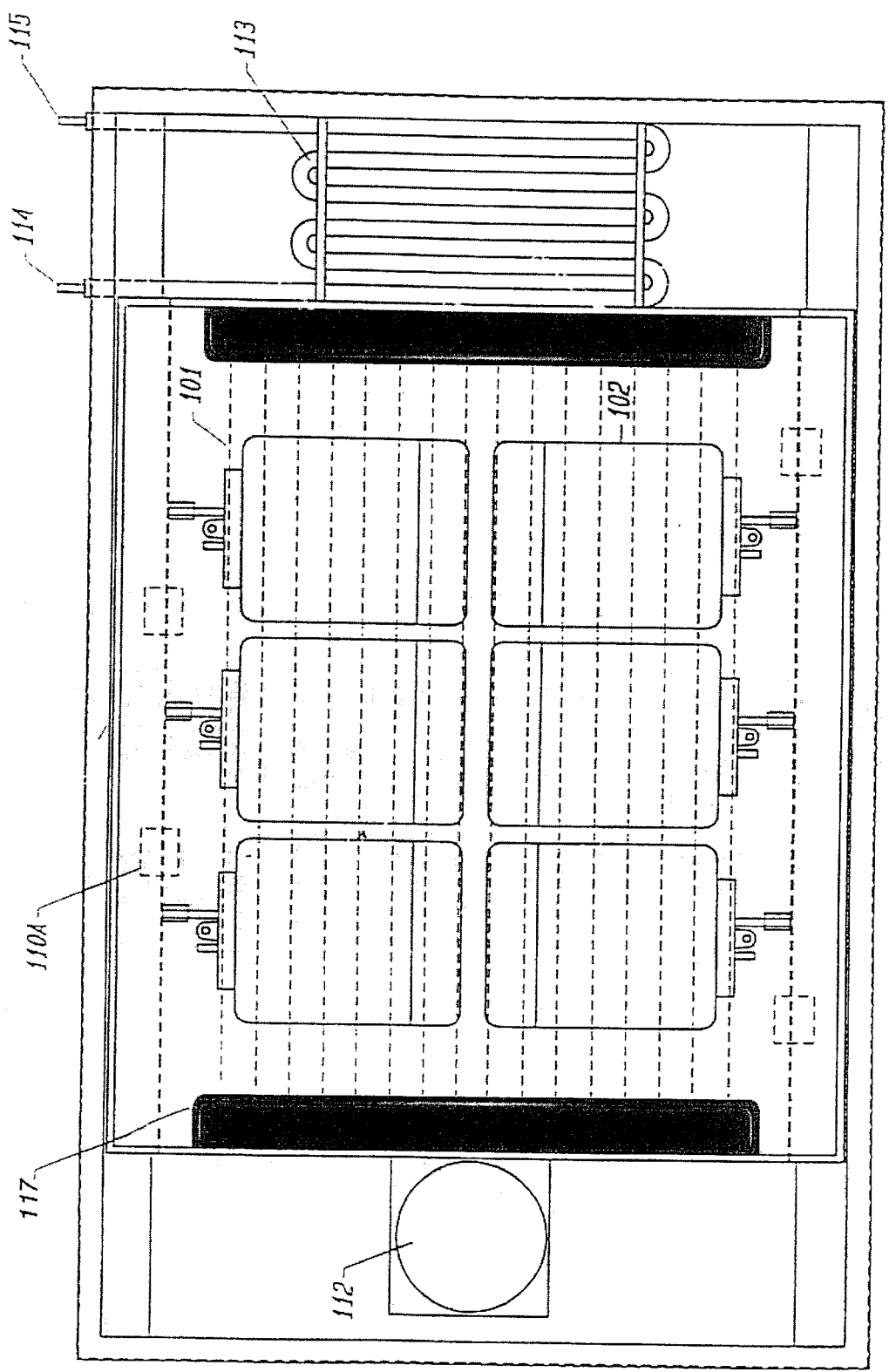
FIG. 8 is another embodiment of FIG. 3.
Figure 9:
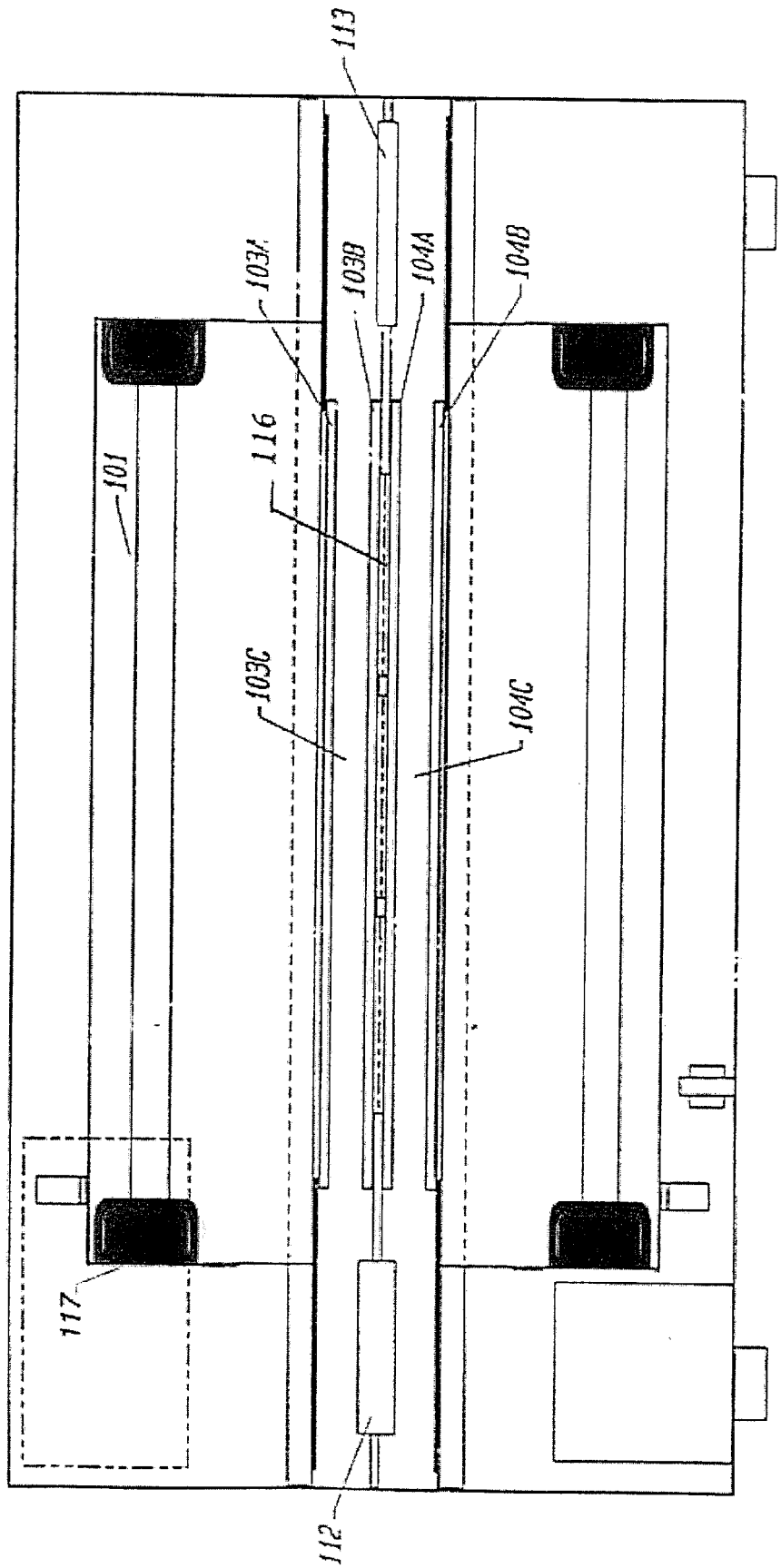
FIG. 9 is another embodiment of FIG. 4.

The present invention further contemplates that the delivery of light from the light sources will be approximately uniform along the length of the light source. Some light sources, particularly long tubular bulbs, display a falloff of output at the ends of the bulbs. The ends also tend to give off the most heat. As shown in FIGS. 8 and 9, to ensure even illumination and a controlled temperature, one embodiment of the present invention has a lip (117) which wraps around the ends of the light sources to block approximately 2–6 cm of the light source on each end from irradiating samples in the device.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal. Because sources of ultraviolet light may vary in flux over a set amount of time, in a preferred embodiment of the present invention, several light output detectors are positioned throughout the device to measure output of the light sources. In one embodiment, the detectors are wired to a feedback control, which can be adjusted to shut off the light source when a certain output level has been reached. This ensures repeatability, which is preferable when inactivating pathogens in blood products. With control of the exposure of light a blood product receives, one can also ensure a sufficient exposure to inactivate pathogens, without having to expose the sample to excess light, which could be damaging.

In designing the devices of the present invention, relative position of the elements of the preferred device have been optimized to allow for fifteen minutes of irradiation time, so that, when measured for the wavelengths between 320 and 350 nanometers, an intensity flux greater than approximately 1 mW cm$^{-2}$, and preferably 15 mWcm$^{-2}$ is provided to the sample vessels. In a preferred embodiment, the device irradiates both sides of the bag.

C. Processing of Large Numbers of Samples

As noted, another important feature of the photoactivation devices of the present invention is that they provide for the processing of large numbers of samples. In this regard, one element of the devices of the present invention is a means for supporting a plurality of blood products, and in particular, blood bags. In the preferred embodiment of the present invention the supporting means comprises glass plates between two banks of lights with a capacity of six 50 ml bags (equivalent to Dupont Stericell™ bag) plus connectors and tubing, at one time. By accepting commonly used commercially available blood bags, the device of the present invention allows for convenient processing of large numbers of samples.

In a preferred embodiment, the plate has a means to position attachments connected to said blood bags, such as tubing and satellite storage bags, so that said attachments do not significantly reduce the intensity of radiation to said blood bags.

D. Temperature Control

As noted, one of the important features of the photoactivation devices of the present invention is temperature control. Temperature control is important because the temperature of the sample at the time of exposure to light can dramatically impact the results. For example, conditions that promote secondary structure in nucleic acids also enhance the affinity constants of many psoralen derivatives for nucleic adds. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

With respect to bacteria, it should be noted that repair of crosslinks occurs during irradiation. However, where a lower temperature is employed during irradiation, the bacterial repair process is suppressed. Thus, a 15° C. irradiation has a significant effect on the level of inactivation that is observed.

Additionally, certain blood preparations can be damaged by small changes in temperature. For example, platelets are best preserved if maintained at 22° C.±2. Thus it is preferred that a photoactivation device for platelets maintain the platelets within or near this range during radiation or the clinical efficacy of the platelets may be reduced.

Without intending to be limited to any particular means of controlling the temperature of blood products during irradiation on the device, in one embodiment the device employs two temperature controlling means. A first temperature controlling means is a means for blowing air from outside of the housing of the device, across the irradiation providing means and back out, to cool them and avoid heat transfer to irradiated samples.

A second temperature controlling means operates in a closed system, cooling and circulating air only from within the system, to avoid the recycling of heat carried in air exhausted from the first temperature controlling means. The second means is for circulating cooled air through the air circulation chamber and within the channel in which the blood bags rest. This second temperature controlling means uses a heat exchanger and a means to circulate the cooled air.

Preferably, the heat exchanger is a conduit, having an inlet port and an outlet port for the circulation of temperature control liquid. The conduit may be covered by a corrugated material with high heat conductivity, which serves to increase the surface area for exchange of heat between the conduit and the air. In one embodiment, the means to circulate air is driven by a DC motor, which produces less ambient heat than an AC motor. Alternatively, the means to circulate air may be driven from outside the housing. Either alternative controls the amount of heat produced within the housing.

Cooled air is circulated over the conduit, across the blood bags which contain the blood products, and through chambers and channels which surround the blood bags. The chambers and channels are also closed off from significant exchange with air originating from outside the housing of the device or air passing over the means from providing electromagnetic radiation, thereby creating "a closed system" that recirculates air. In an alternative embodiment, the present invention contemplates that the second temperature controlling means comprises a refrigeration unit installed within the housing of the photoactivation device.

Air circulating in the second temperature control means does not mix with air blowing through the first temperature control means. This separation of temperature control allows the samples to be cooled appropriately.

In one embodiment, the device of the present invention comprises a shaking means, such as a shaker or an agitator, giving the samples horizontal unidirectional and sinusoidal motion of variable frequency and amplitude. The use of a shaking means during irradiation with the device is contemplated for maintaining an even temperature throughout the samples within the blood bags by providing mixing of a sample in the blood bags during irradiation. Additionally, use of a shaker for platelet samples reduces platelet activation during storage. In one embodiment, a shaker is positioned within the housing of the irradiation device, moving the samples by contacting the blood bag supporting means directly. It is contemplated that the top plate of the lower plate assembly may not be fixed with respect to the rest of the lower plate assembly, thus allowing a shaker to contact the top plate directly to achieve agitation. Also contemplated is the movement of the entire lower plate assembly by a shaker. Alternatively a shaker may be positioned outside the housing, moving the samples by moving the entire housing of the device. The present invention contemplates the use of a ridged upper surface on the blood bag supporting means which provides friction sufficient to maintain the position of the sample blood bags during shaking.

In another embodiment, heat from the lamps, ballasts and other sources is kept away from the blood bags by one or several partition between the various sources of heat and the bags. This further assists in maintaining a biologically acceptable temperature in the samples.

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e. an opaque housing). No irradiation is allowed to pass to the user. This allows for inherent safety for the user.

F. Sample Containers

The material of the container which holds the sample to be irradiated in the irradiation device can effect how well the irradiation device operates. The material used can effect the penetration of radiation to the sample and the amount of scatter of radiation impinging on the container. The sample container of one embodiment of the present invention is a blood bag made of a plastic transparent to ultraviolet light, preferably Teflon (available from American Fluroseal, Silver Spring, Md.). Some other acceptable plastic components are ethyl vinyl acetate (bags available from Terumo, Japan); poly (vinyl chloride) (PVC) (bags available from Baxter Travenol or Cutter, Covina, Calif.), which may be combined with plasticisers; or polyolefin (bags available from the Fenwal Division of Baxter Travenol Laboratories, Inc., Deerfield, Ill.). For PVC, contemplated placticisers are di (2-ethylhexyl) phthalate (DEHP), tri (2-ethylhexyl) trimellitate (TEHTM). The present invention, however, is not intended to be limited to any composition of blood bag, but contemplates the use of any bag that is somewhat transparant to ultraviolet light. The material may also effect concentration of components in the sample to be irradiated. In a preferred embodiment, the sample is irradiated on the irradiation device in a bag that does not bind a significant percent of photoreactive compound contained in the sample.

The parameters of the container also control to some extent how the sample is affected during the irradiation. For example, a blood bag for platelet storage preserves platelets better if its walls are thin enough to allow the transfer of sufficient oxygen to prevent the increased rate of lactate production which causes decreased platelet viability. Carmen, R., "The Selection of Plastic Materials for Blood Bags," Transfusion Med. Rev. 7:1 (1993).

The nature of the blood product may have an impact on efficiency. Red cells, for example, absorb different wavelengths of light than do platelets. Red cells may reduce the efficiency of irradiation due to blocking of light. Therefore, platelets contaminated with red. cells may see a lower intensity of light than platelet preparations containing no red blood cells.

As pointed out above, changes in intensity can impact photoactivation results, and these changes can result from changes in distance within the sample through which the radiation must travel. The thickness of the sample, as defined by the walls of the blood bag, and the volume of the blood product, also effect how much light can reach the sample. In a preferred embodiment of the present invention, when the blood bag containing the sample for irradiation rests within the radiation device, it forms a film of blood product which has a "central path length" of between approximately 0.1 and 4 cm. A "central path length" is here defined as the shortest distance between two walls of a blood bag that passes through the center of the bag. In one embodiment, the "central path length" of the sample is a fixed value for all bags used. This provides reproducibility and repeatability. In a preferred embodiment, a shaker is employed, to provide movement, or slushing, of the sample material so that each part of the sample is brought to the surface of the blood bag during irradiation. This may allow for variation in the central path lengths of the bags, while preserving reproducibility and repeatability, because the agitation may cycle the sample to the surface of the blood bag. Therey, it is ensured that sufficient light can reach the samples regardless of the central path length. In another preferred embodiment, no other pressure need be exerted on the bag by the radiation device, or any other source, other than the force of gravity, to obtain the preferred "central path length." In one embodiment, the upper and lower plate assemblies are separated by between approximately 1 and 10 cm, to accommodate bags having a central path length within that range.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); ° C. (degrees Centigrade); HPLC (High Pressure Liquid Chromatography).

EXAMPLE 1

As noted above, the present invention contemplates devices and methods for the activation of photoreactive nucleic acid binding compounds. In this example, a photoactivation device is described for decontaminating blood products according to the method of the present invention. This device comprises: a) means for providing appropriate wavelengths of electromagnetic radiation to cause activation of at least one photoreactive compound; b) means for supporting a plurality of blood products at a fixed distance from the radiation providing means during activation; and c) means for maintaining the temperature of the blood products within a desired temperature range during activation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (100) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

Figure 2:
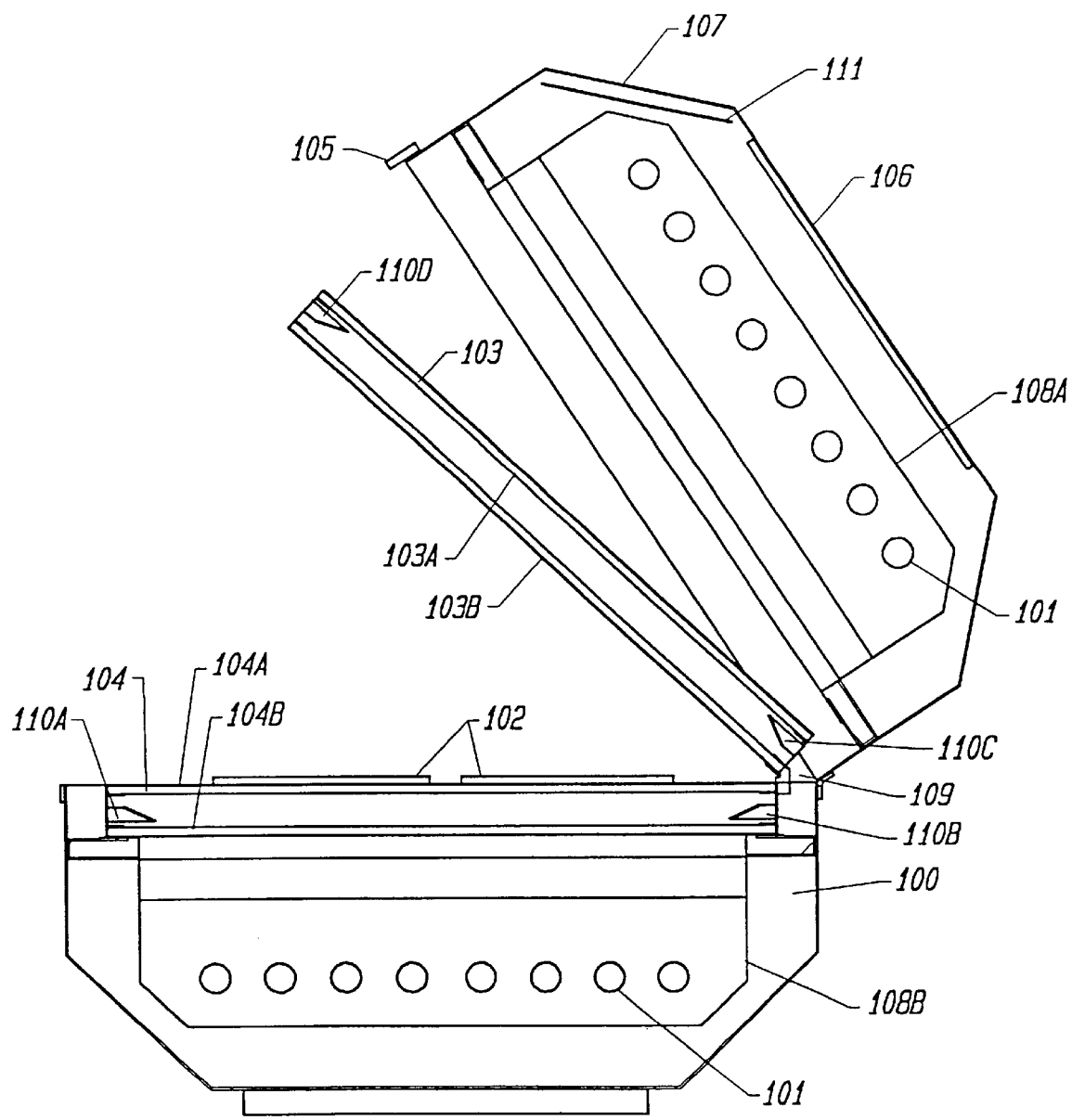
FIG. 2 is a cross-sectional view of the device shown in FIG. 1, in the open position, along the lines of 2—2.

FIG. 2 is a cross-sectional view of the device shown in FIG. 1 along the lines of 2—2. FIG. 2 shows the arrangement of the bulbs (101) with the housing (100) opened. A reflecting means (108A, 108B) completely surrounds each array of bulbs (101). Blood product containing means (102) are placed between upper (103) and lower (104) ultraviolet light transparent plate assemblies. When the upper plate assembly (103) is lowered over the lower plate assembly (104), the upper (103) and lower (104) plate assemblies define a channel (116—not show in this figure) through which air can be circulated to cool the blood product containing means. Each plate assembly is comprised of top (103A, 104A) and bottom (103B, 104B) plates. The plate assemblies (103, 104) are connected via a hinge (109) which is designed to accommodate the space created by the blood product containing means (102). The upper plate assembly (103) is brought to rest just above the top of the blood product containing means (102) supported by the bottom plate (104B) of the lower plate assembly (104). In an alternative embodiment, the upper plate assembly (103) may be in a fixed relationship with the housing (100) and the entire top part of the housing, including the upper plate assembly (103) can be brought to rest just above the top of the blood product containing means (102).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

Figure 3:
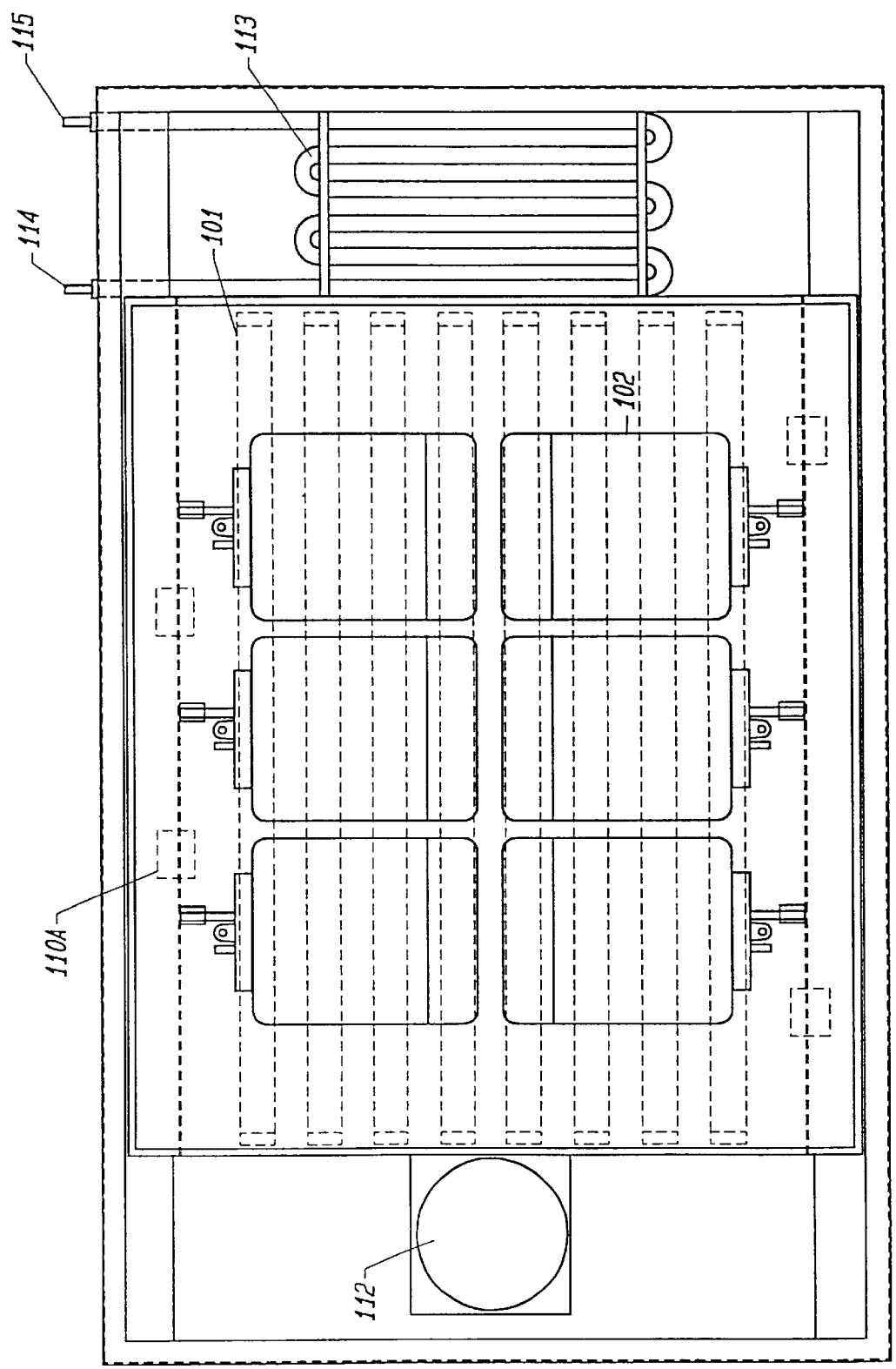
FIG. 3 is a cross-sectional view of the device shown in FIG. 1 along the lines of 3—3.

FIG. 3 is a cross-sectional view of the device shown in FIG. 1 along the lines of 3—3. Six blood product containing means (102) (e.g. Teflon™ platelet unit bags) are placed in a fix relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

Figure 4:
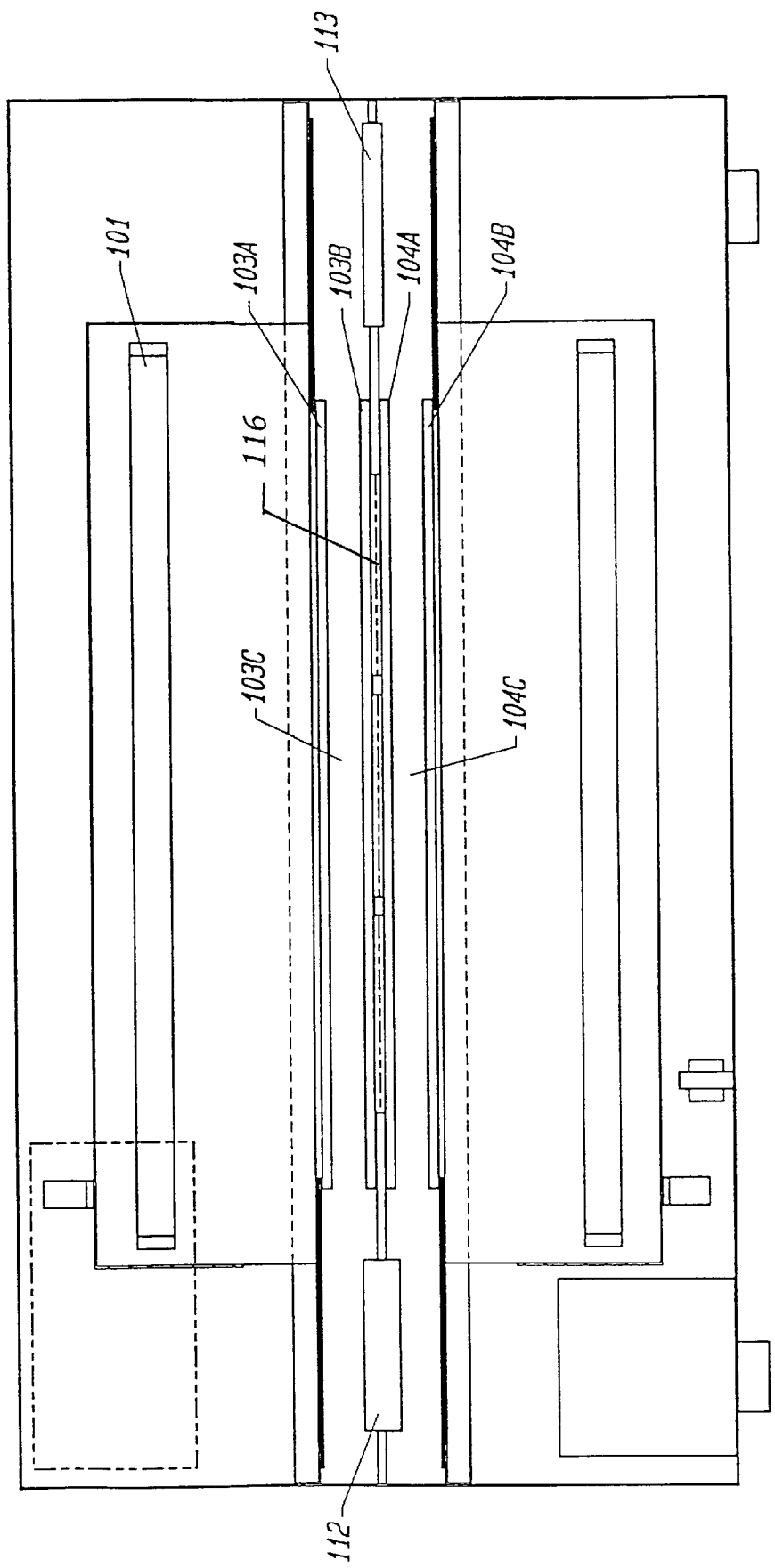
FIG. 4 is a cross-sectional view of the device shown in FIG. 1 along the lines of 4—4.

FIG. 4 is a cross-sectional view of the device shown in FIG. 1 along the lines of 4—4. FIG. 4 more clearly shows the temperature control approach of a preferred embodiment of the device. When the upper plate assembly (103) is lowered over the lower plate assembly (104), the upper (103) and lower (104) plate assemblies define a channel (116) bordered by the bottom plate (103B) of the upper assembly (103) and the top plate (104A) of the lower assembly (104). Upper plate assembly plates (103A, 103B) and lower plate assembly plates. (104A, 104B) each define an air circulation chamber (103C, 104C), respectively. The fan (112) can circulate air within the chambers (103C, 104C). When the heat exchanger (113) is employed, the circulating air cooled and passed between the plates (103A, 103B, 104A, 104B) within the air circulation chambers (103C, 104C), by the fan (112) and then returned to the heat exchanger (113) through the channel (116) between the upper (103) and lower (104) plate assemblies, thereby cooling the blood product containing means. The circulating air is kept within a dosed system when the housing (100) is in the closed position, comprising the channel (116), the air circulation chambers (103C, 104C) and the surface of the heat exchanger (113) and the fan (112). The air within the closed system does not mix or exchange with the air outside the housing or within the housing which is not part of the closed system, such as the area surrounding the bulbs (101).

EXAMPLE 2

Figure 5:
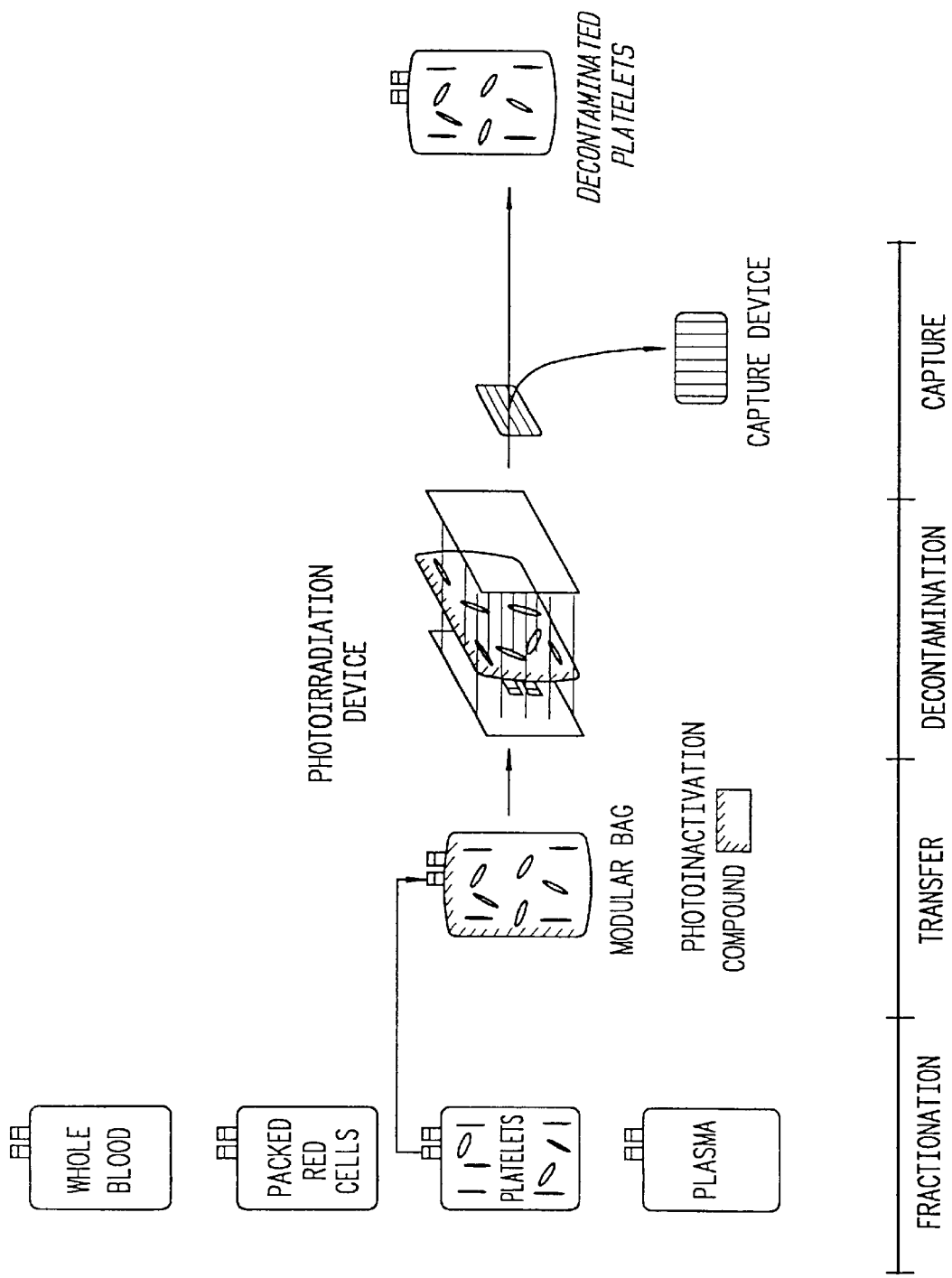
FIG. 5 schematically shows the decontamination approach of the present invention applied specifically to blood products.

FIG. 5 shows an embodiment wherein platelets are treated by the method of the present invention. Following fractionation, platelets are transferred to a bag containing a nucleic acid binding compound (shown in FIG. 1 as a shaded bag). This bag, which has transmission properties and other characteristics suited for the present invention, is then placed in an irradiation device (such as that described in Example 1, above) and is irradiated. The free compound may be collected or "captured" as desired by a capture device. In such a case, the bag would contain only compound that is contained in cells; the bag would have no free compound (this bag is indicated in FIG. 1 as unshaded).

EXAMPLE 3

In this example, the decontamination methods of the present invention are applied to inactivate *Yersinia enterocolitica* wild type, serotype 3 biotype 4. This organism is found in blood products. See generally R. Y. Dodd, In: *Transfusion Medicine in the* 1990's (American Assoc. Blood Banks 1990) (S. J. Nance, ed.). See also B. J. Grossman et al., Transfusion 31:500 (1991).

An overnight culture of the organism was made by inoculating 10 ml of brain-heart infusion (BHI) broth from a motility stab. This was maintained at 35° C. and 0.1 ml of it was used to inoculate 20 ml of BHI broth for use in the experiment. After overnight incubation at 35° C., the stationary culture was pelleted for 15 minutes at 1900 g, the supernatant was discarded, and the bacterial pellet was resuspended in 1 ml of heat-inactivated normal serum pool. This was infused into a freshly expired unit of human platelets obtained from the Blood Bank of Alameda-Contra Costa Medical Association. 5 ml aliquots of bacteria containing platelet concentrate were drawn from the bag and received specified amounts of 8-MOP and UVA irradiation, except for the controls, which were irradiated without psoralen, or received no treatment (see Table 2). Temperature was maintained at 25° C. during irradiation by placing the platelet concentrate in stoppered glass water-chambers jacketed chambers attached to a circulating water bath. The irradiation device (Derma Control, Dolton, Ill.; Model No. 1224-Special) employed two arrays (six lamps/array spaced at 2.5 inches), one array above the sample and one bank below the sample (the sample is thus approximately 3 inches from the lamps). Each array is separated from the other by approximately six inches, has a polished metal reflector behind it, and is covered by a UVA-transmitting acrylic plastic sheet. The sample to be processed (e.g. platelet bag) sits on the lower sheet.

TABLE 2

| | drug | 8-MOP/ml | irr. time (min) | log/ml | −titer |
|---|---|---|---|---|---|
| 1 | no drug | | 0 | 9.1 | |
| 2 | no drug | | 10 | 9.3 | 0.2 |
| 3 | 8-MOP | 30 ug | 10 | <0 | >−9.1 |
| 4 | 8-MOP | 10 | 10 | <0 | >−9.1 |
| 5 | 8-MOP | 3 | 10 | 3.4 | −5.7 |
| 6 | 8-MOP | .2 | 10 | 6.8 | −2.3 |
| 7 | 8-MOP | .06 | 10 | 9.0 | −0.1 |

Derma Control F587T12-BL-HO type bulbs were used. These are "black light" tubes (engineered to emit specific wavelengths by means of an internal phosphor coating) 24 inches in length. The peak wavelength is below 360 nm, unlike simple mercury lamps or common "BLB" fluorescent bulbs. Total intensity is less than 20 mW/cm$^2$.

Bacteria were quantified by plating 0.1 ml of serial 10-fold dilutions in BHI broth onto 100 mm petri dishes containing BHI agar. After 24 hr incubation at 35° C., colonies were counted and bacterial concentration was calculated on a per ml basis. The results (Table 2) show that as little as 3 ug/ml of 8-MOP is able to inactivate almost six logs of bacteria. With 10 ug/ml, ten minutes provide more than enough irradiation. Indeed, with 10 ug/ml, five minutes of irradiation appears to be adequate.

EXAMPLE 4

Artuc and co-workers examined the solubility of 8-MOP in human and bovine serum proteins, and showed that at 8-MOP concentrations ranging from 100 to 1000 ng/ml. concentrations similar to those observed in patients undergoing psoralen ultraviolet A (PUVA) therapy for psoriasis, 75% to 80% of the 8-MOP was bound to albumin. M. Artuc et al., Brit. J. Derm. 101:669 (1979).

In this example, the binding of 8-MOP to Calf Thymus DNA is compared using plasma and a protein free medium in order to validate the efficiency of psoralen-nucleic interactions under the decontamination methods of the present invention. Although this measurement used eukaryotic nucleic acid rather than bacterial nucleic acid, it is a useful indicator of the degree of adduct formation for bacteria.

$^3$H-8-MOP was prepared to a concentration of 115 ug/ml in ethanol at a specific activity of 4.7×10$^6$ CPM/microgram (hereinafter "8-MOP stock"). Thereafter 130.5 or 22 ul of 8-MOP stock (2 each) for samples containing DNA("+DNA") and 52.2 or 8.7 ul for samples not containing DNA ("−DNA") were dried down. To +DNA samples, 40 ul of DNA stock (7.7 mg/ml) was added as well as either 460 ul plasma (day old frozen) or 450 ul Tris-EDTA ("TE") buffer. To the latter was also added 10 ul 5M NaCl. For − DNA samples (i.e. the controls), 184 ul plasma and 16 ul water was added.

The samples were mildly vortexed for approximately one hour and the counts were checked to confirm that the 8-MOP dissolved.

Each sample (100 ul) was irradiated on an HRI-100 (HRI Research Inc., Concord, Calif.) at 25° C. for 0, 2, 4, 8, and 16 minutes. Samples were kept at 4° C. overnight after irradiation. Thereafter, the samples were extracted. First, a phenol solution was prepared at pH 8 by equilibrating with 0.1 M Tris pH 8. Each sample was then extracted with 100 ul phenol. Each sample was centrifuged for 5 minutes to remove the aqueous phase to a new tube. A second extraction was performed with 100 ul 1:1 phenol:chloroform. A final extraction was performed with 100 ul chloroform.

The final aqueous phase was precipitated by adding 50 ul NaCl adjusted to give a final concentration of NaCl of 0.2 M and then adding 250 ul ethanol. The samples were again centrifuged (10 minutes). The supernatant was removed and the pellets were dried. The pellets were resuspended in 100 ul TE and re-precipitated. This was repeated for a total of 3 precipitations. The final pellets were brought up in 600 ul water and 100 ul was counted. Each sample was assayed for DNA by measuring absorbency (260 nm). 8-MOP levels were plotted as adducts per 1000 base pairs ("8-MOP:kBP").

Figure 6:
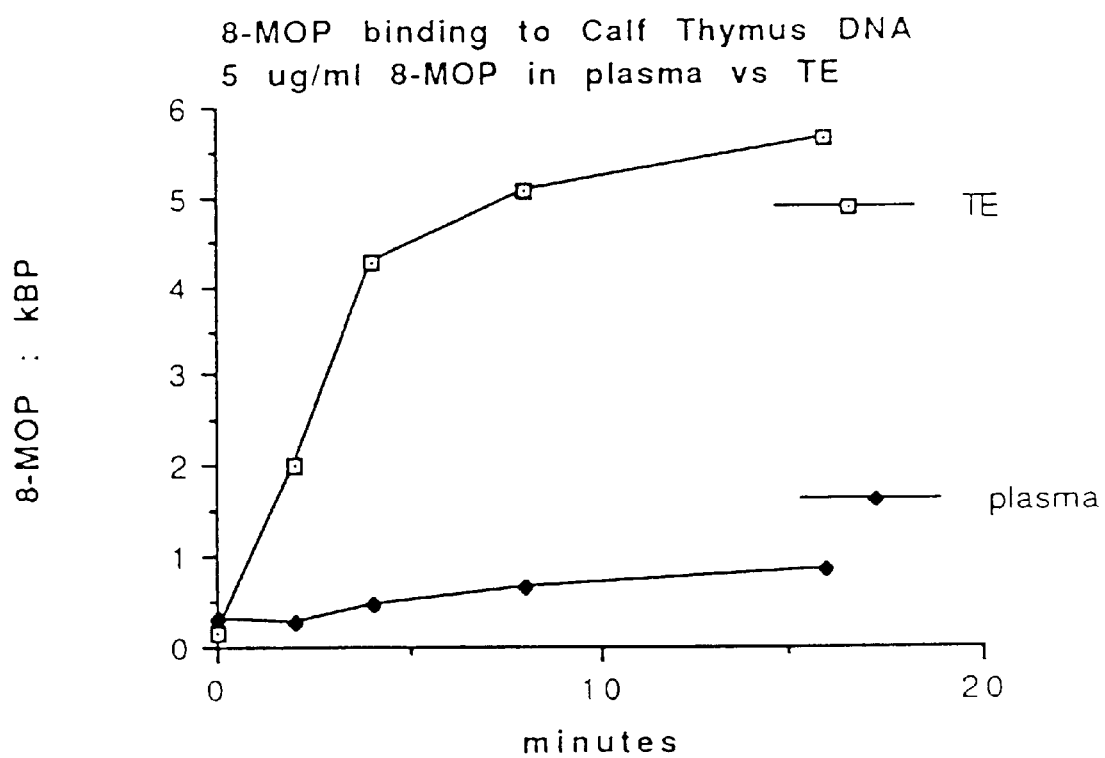
FIG. 6 is a graph showing the photoaddition of 8-methoxypsoralen to nucleic acid.

The results (FIG. 6) show that plasma does significantly change the addition kinetics of 8-MOP to DNA. Addition to nudeic acid is much better in the protein free media.

The frequency of 8-MOP-DNA adduct formation in protein free media predicts a high multiplicity of modification of the bacterial genome. Furthermore, this type of biochemical measurement has the potential to provide a means to monitor the efficiency of the photochemical inactivation method.

EXAMPLE 5

Photoactivation of psoralens and isopsoralens may result in a variety of photoproducts. "Photoproduct" is best understood by considering the possible reactions of photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

$$C \rightarrow C^*$$

What happens next is largely a function of what potential reactants are available to the excited species. Since it is short-lived, a reaction of this species with nucleic acid ("NA") is believed to only be possible if nucleic acid is present at the time the excited species is generated.

Thus, the reaction must, in operational terms, be in the presence of activating wavelengths of electromagnetic radiation, i.e. it is "photobinding"; it is not dark binding. The reaction can be depicted as follows:

$$C^* + NA \rightarrow NA:C$$

The product of this reaction is hereinafter referred to as "Photoaddition Product" and is to be distinguished from "Photoproduct."

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

$$C^* \rightarrow C$$

On the other hand, the excited species may react with itself (i.e. a ground state or excited species) to create a ground state complex ("C:C"). The product of these self-reactions where two compounds react is referred to as "photodimer" or simply "dimer." The 'self-reactions, however, are not limited to two compounds; a variety of multimers may be formed (trimers, etc.).

The excited species is not limited to reacting with itself. It may react with its environment, such as elements of the solvent ("E") (e.g. ions, gases, etc.) to produce other products:

$$C^* + E \rightarrow E:C$$

It is this type of reaction that is believed to cause cellular damage (e.g., reaction with oxygen to create singlet oxygen species). Furthermore, it may simply internally rearrange ("isomerize") to a ground state derivative ("["):

$$C^* \rightarrow [$$

Finally, the excited species may undergo other reactions than described here.

The present invention and the understanding of "photoproduct" does not depend on which one (if any) of these reactions actually occurs. "Photoproduct" —whatever its nature—is deemed to exist if, following the reaction of a compound and activating wavelengths of electromagnetic radiation, there is a resultant product formed that can interact with other components of the reaction environment.

With psoralens such as 4'-hydroxymethyl-4,5',8-trimethylpsoralen (HMT), there is a number of resultant products produced when the HMT is exposed to activating wavelengths of electromagnetic radiation. The major resultant products of HMT are two cyclobutyl photodimers. In one of the dimers, the two pyrone rings are linked in a cis-syn configuration, while in the other dimer, the linkage occurs between the furan end of one molecule and the pyrone end of the other, again with cis-syn configuration. A third resultant product of HMT is a monomeric HMT photoisomer. In this isomer, the central ring oxygens assume a 1, 4 instead of the normal 1, 3 orientation. While the two photodimers would not be expected to have an intercalating activity due to geometrical considerations, the photoisomer remains planar, and accordingly, it is contemplated that it has a positive intercalative association with double stranded nucleic acid and, thus, could be a mutagen.

In this example, the photochemical breakdown of 8-MOP is compared with AMT. The samples were analyzed by reverse phase HPLC using a Rainen Dynamax 300A column. Gradient elution was performed with 0.1 M ammonium acetate/acetonitrile (0–70% acetonitrile over 42 minutes). AMT elutes as a single peak at approximately 24 minutes under these conditions. Detection was by absorption at either 260 or 330 nm. The latter wavelength was used for the plasma containing samples.

Standard solutions of each compound were prepared at various concentrations. These solutions were then diluted 1:10 into water, then 300 ul injected for analysis. All samples were monitored at 300 run. Peaks were analyzed by measuring either peak height or peak area, then converted to a gh/ml value using the standard plot. Peak area was determining by photocopying the trace, cutting out the copy of the peak, then weighing the resultant trace. The two methods gave essentially the same result.

Figure 7:
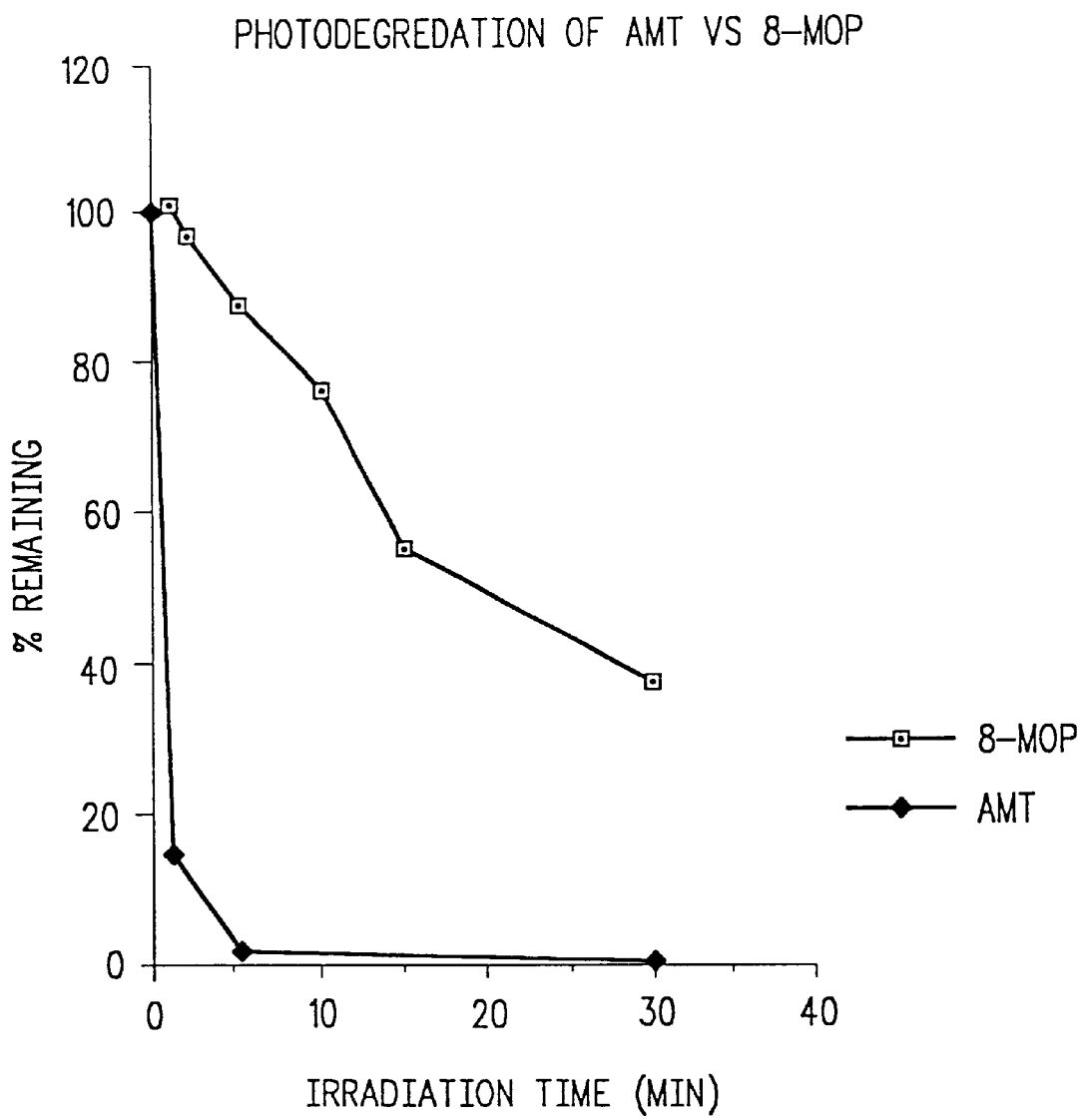
FIG. 7 is a graph showing the degradation of 8-methoxypsoralen (8-MOP) compared to that of 4'-aminomethyl-4,5',8-trimethylpsoralen (AMT), as measured by HPLC.

The results are shown in FIG. 7. Clearly, AMT degrades more quickly than 8-MOP. It would, therefore, be expected to generate more photoproducts—which eventually would end up in the transfusion recipient. By contrast, it is not expected that 8-MOP generates a significant amount of photoproducts. This is important when one considers that the weight of authority has concluded that non activated 8-MOP is not mutagenic.

EXAMPLE 6

When platelets become activated, an alpha granule membrane glycoprotein called GMP140 becomes exposed on the platelet surface. Less than (5%) of fresh, normal unstimulated platelets express detectable GMP 140 levels by flow cytometry. See generally M. J. Metzelaar, *Studies on the Expression of Activation-Markers on Human Platelets* (Thesis 1991).

To measure GMP140, a small aliquot of platelet rich plasma is placed in HEPES buffer containing a GMP140-binding antibody or control mouse IgG. CD62 is a commercially available monoclonal antibody which binds to GMP 140 (available from Sanbio, Uden, the Netherlands; Caltag Labs, So. San Francisco, Calif., and Becton Dickinson, Mountain View, Calif.). After a fifteen minute incubation, Goat Anti-Mouse IgG conjugated to FITC is added to the tube in saturating amounts. Finally, the cells are diluted in isotonic saline, fixed with paraformaldehyde and analyzed on a FACSCAN™ (Becton Dickinson, Mountain View, Calif.). The positive control is made by adding Phorbol Myristate Acetate (PMA) to the test system at a final concentration of $10^{-7}M$.

In this example, CD62 was employed to measure the impact, if any, of irradiation alone on platelet activation. The antibody was stored in small aliquots (0.01 mg/ml) at $-40°$ C. prior to use. A mouse IgG control (0.05 mg/ml) (Becton Dickinson, Mountain View, Calif. #9040) 5X concentrated was employed. At time of use, this was diluted 1:5 in HEPES buffer. The secondary antibody was goat Anti-Mouse IgG conjugated to FITC (TAGO, Burlingame, Calif. #3506). This was stored in small aliquots at −20° C. Phorbol Myristate Acetate (PMA) (Sigma, St. Louis, Mo.) was stored at −40° C. At time of use, this was dissolved in DMSO (working concentration was $1.62 \times 10^{-5}$ M).

16%. Paraformaldehyde (PFA) (Sigma, St. Louis, Mo.) was prepared by adding 16 grams paraformaldehyde to 100 ml de-ionized water. This was heated to 70° C., whereupon 3 M NaOH was added dropwise until the solution was clear. The solution was cooled and the pH was adjusted to 7.4 with 1 N HCl. This was filtered and stored. A commercially available isotonic buffer was used: Hematall Isotonic Diluent (Fisher # CS 606-20).

For measuring platelet activation of platelet concentrates, a unit of human platelets was obtained from the Blood Bank of Alameda-Contra Costa Medical Association. 5 ml aliquots were drawn from the bag and received specified amounts of UVA irradiation, except for the control, which received no treatment other than being placed in a chamber for irradiation. Temperature was maintained at 25° C. during irradiation by placing platelet concentrate in stoppered glass water-jacketed chambers attached to a circulating water bath. The irradiation device (Derma Control, Dolton, Ill.; Model No. 1224-Special) was as described in Example 3, above. Following irradiation, the platelets were stored for 5 days. At specific time points, aliquots were taken and processed.

Processing involved adding an aliquot (e.g. 5 microliters) of platelet concentrate to each microcentrifuge tube containing the antibody and appropriate reagents and this was mixed very gently by vortex. The samples were incubated for 15 minutes at room temperature.

The Goat anti-Mouse IgG-FITC (diluted 1:10 in HEPES buffer) was added (5 microliters) to each tube and the solution was mixed by gentle vortex. The samples were incubated for an additional 15 minutes at room temperature.

Isoton II was added (1ml) to each tube and mixed gently with a polypropylene disposable pipette. 8% PFA in HEPES (150 microliters) was added to each diluted sample to final 1%. The platelets were analyzed on the FACSCAN™. The results are shown in Table 3.

TABLE 3

| | Day 3 | | Day 5 | |
| --- | --- | --- | --- | --- |
| Conditions | Unactivated | PMA Activated | Unactivated | PMA Activated |
| Control | 17 | 85 | 25 | 89 |
| UV 5' | 17 | 87 | 24 | 86 |
| UV 10' | 51 | 84 | 77 | 79 |

Activation is expressed as a percent. Clearly, irradiation for ten minutes (UV 10') resulted in a significant negative impact on stored platelets; the platelets were highly activated. By contrast, irradiation for five minutes (UV 5') resulted in no significant activation above the control which received no irradiation.

EXAMPLE 7

Given the results of Example 6, it is clear that either a shorter irradiation time or the use of filters is needed to avoid damage to cells by UV irradiation. In this example, CD62 is employed to measure the impact of irradiation in the presence of psoralen on platelet activation. Shorter irradiation times and wavelength filters are separately employed.

Shorter Irradiation Times

A unit of human platelets was again obtained from the Blood Bank of Alameda-Contra Costa Medical Association. 5 ml aliquots were drawn from the bag to receive five minutes (5') of UVA irradiation in the presence of 10 ug/ml 8-MOP, except for the control, which received no treatment other than being placed in a chamber for irradiation. Temperature was maintained at 25° C. during irradiation by placing platelet concentrate in stoppered glass waterjacketed chambers attached to a circulating water bath. The irradiation device (Derma Control, Dolton, Ill.; Model No. 1224-Special) was as described in Example 3, above.

Following irradiation, the platelets were again stored for 5 days as in Example 6. At specific time points, aliquots were taken and assayed with the CD62 antibody and analyzed on the FACSCAN™ to show that, under these conditions, platelets can be inactivated without damage to the cells and stored for five days prior to transfusion.

Wavelength Filters

An aqueous solution of $Co(No_3)_2$ was used in combination with $NiSO_4$ to substantially remove the 365 nm component of the emission spectrum of the light source employed. The Co—Ni solution can be conveniently used in place of water as a coolant during the irradiation.

Following a ten minute irradiation with the filter, the platelets were stored an assayed with the CD62 antibody on the FACSCAN™ to show that, under these conditions, platelets can be inactivated without damage to the cells and stored for five days prior to transfusion.

The above has been offered for illustrative purposes only, and is not intended to limit the scope of the invention of this application, which is as defined in the claims below.

What is claimed is:

1. A device, comprising:
   i) a fluorescent source of electromagnetic radiation comprising a plurality of tubular bulbs, each of said bulbs having first and second ends and a middle region;
   ii) a blood bag support configured such that at least a portion of said electromagnetic radiation from said bulbs contacts a blood bag when positioned on said support; and
   iii) a means for allowing said contact of electromagnetic radiation from at least a portion of said middle region while preventing said contact of electromagnetic radiation from at least a 2 cm portion of each of said first and second ends.

2. The device of claim 1, wherein said means comprises a first lip which wraps around the first ends of said bulbs and a second lip which wraps around said second ends of said bulbs.

3. The device of claim 1, wherein said blood bag support is dimensioned to permit a plurality of blood bags to be supported for irradiation.

4. The device of claim 3, wherein said blood bag support further comprises means to position a plurality of attachments connected to said blood bags, so that said attachments do not significantly reduce the intensity of radiation to said blood bags.

5. The device of claim 1, wherein said contact of electromagnetic radiation further comprises wavelengths between 320 and 400 nm.

6. A device, comprising:

i) a fluorescent source of electromagnetic radiation comprising a plurality of tubular bulbs, each of said bulbs having first and second ends and a middle region;

ii) a blood bag support configured such that at least a portion of said electromagnetic radiation from said bulbs contacts a blood bag when positioned on said support; and iii) an opaque material positioned around the ends of the bulbs to allow said contact of electromagnetic radiation from at least a portion of said middle region while preventing said contact of electromagnetic radiation from at least a 2 cm portion of each of said first and second ends.

7. A device, comprising:

i) a fluorescent source of electromagnetic radiation comprising a plurality of tubular bulbs, each of said bulbs having first and second ends and a middle region, wherein the first and second ends generate substantially more heat than the middle region;

ii) a blood bag support configured such that at least a portion of said electromagnetic radiation firm said bulbs contacts a blood bag when positioned on said support; and iii) a means for controlling the temperature of the blood bag when positioned on said support by allowing said contact of electromagnetic radiation from at least a portion of said middle region while preventing at least a portion of the heat generated from each of said first and second ends from contacting the blood bag.

8. The device of claim 7, wherein said means comprises a first lip which wraps around the first ends of said bulbs and a second lip which wraps around said second ends of said bulbs.

* * * * *